United States Patent
Chen et al.

(10) Patent No.: US 6,248,527 B1
(45) Date of Patent: Jun. 19, 2001

(54) METHOD OF DETECTING RISK OF TYPE II DIABETES BASED ON MUTATIONS FOUND IN CARBOXYPEPTIDASE E

(75) Inventors: Hong Chen, Brookline; Joanne Meyer, Marlborough, both of MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/233,989

(22) Filed: Jan. 19, 1999

Related U.S. Application Data

(60) Provisional application No. 60/105,102, filed on Oct. 21, 1998.

(51) Int. Cl.[7] .............................. C12Q 1/68; C07H 21/02; C07H 21/04; C07K 1/00
(52) U.S. Cl. ............................ 435/6; 536/23.1; 536/23.2; 530/350
(58) Field of Search .......................... 435/4, 6; 536/23.1, 536/23.2, 23.5

(56) References Cited

U.S. PATENT DOCUMENTS 5,470,873 * 11/1995 Ji-Won Yoon ........................ 514/460
5,593,837 * 1/1997 Naggert et al. ......................... 435/6

OTHER PUBLICATIONS

Walker et al., Mammalian genomics, vol. 8, p. 783–784, Nov. 1997.*
Maddatu et al., Mammalian Genomics, vol. 8, 857–858, Nov. 1997.*
Utsunomiya et al., Diabetologia, vol. 41(6), p. 701–705, Jun. 1998.*
Manser et al. (1990), "Human Carboxypeptidase E, Isolation and Characterization of the cDNA, Sequence Conservation, Expression and Processing In Vitro", *Biochem. J.* 267:517–525.
Carroll et al. (1988), "A Mutant Human Proinsulin Is Secreted from Islets of Langerhans in Increased Amounts Via an Unregulated Pathway", *Proc. Natl. Acad. Sci. USA* vol. 85:8943–8947.
Fricker (1988), "Activation and Membrane Binding of Carboxypeptidase E", *Journal of Cellular Biochemistry* 38:279–278.
Varlamov et al., (1995), "The C–terminal Region of Carboxypeptidase E Involved in Membrane Binding Is Distinct from the Region Involved with Intracellular Routing", *The Journal of Biological Chemistry* 271 (11):6077–6083.
Naggert et al. (1995), "Hyperproinsulinaemia in Obese Fat/Fat Mice Associated with a Carboxypeptidase E Mutation which Reduces Enzyme Activity", *Nature Genetics* 10:135–141.
Varlamov et al. (1996), "Induced and Spontaneous Mutations at $Ser^{202}$ of Carboxypeptidase E", *The Journal of Biological Chemistry* 271(24):13981–13986.
Fricker et al. (1996), "Carboxypeptidase E Activity Is Deficient in Mice with the Fat Mutation", *The Journal of Biological Chemistry* 271 (48):30619–30624.
Irminger et al. (1997), "Proinsulin Targeting to the Regulated Pathway Is Not Impaired in Carboxypeptidase E–deficient $Cpe^{fat}Cp^{fat}$ Mice", *The Journal of Biological Chemistry* 272 (44):27532–27534.
Utsunomiya et al. (1998), "Organization of the Human Carboxypeptidase E Gene and Molecular Scanning for Mutations in Japanese Subjects with NIDDM or Obesity", *Diabetologia Springer–Verlag* 701–705.

* cited by examiner

Primary Examiner—Karen M. Hauda
Assistant Examiner—Shin-Lin Chen
(74) Attorney, Agent, or Firm—Alston & Bird LLP

(57) ABSTRACT

The invention is directed to methods for diagnosing Type II diabetes or the risk for developing Type II diabetes by detecting alterations in expression, sequence, or function of carboxypeptidase E nucleic acid or protein. The invention is also directed to methods for preventing or treating Type II diabetes by modulating the levels, altering the sequence, or controlling the function of carboxypeptidase E nucleic acid or protein. The invention is also directed to methods for identifying agents that modulate the levels or affect the function of carboxypeptidase E nucleic acid or protein. The invention is also directed to methods using the agents to treat or diagnose Type II diabetes. The invention is also directed to animal models of Type II diabetes using the carboxypeptidase E gene. The invention is also directed to compositions based on carboxypeptidase E nucleic acid or protein useful for treating or diagnosing diabetes, identifying compounds for treating or diagnosing diabetes, and developing animal models of diabetes.

6 Claims, 8 Drawing Sheets

| 1 | GGCGTGCCCG | TCTCTCCGCC | GGCCCCCTGC | CTCGCAGTGG |
|---|---|---|---|---|
| 41 | TTTCTCCTGC | AGCTCCCCTG | GGCTCCGCGG | CCAGTAGTGC |
| 81 | AGCCCGTGGA | GCCGCGGCTT | TGCCCGTCTC | CTCTGGGTGG |
| 121 | CCCCAGTGCG | CGGGCTGACA | CTCATTCAGC | CGGGGAAGGT |
| 161 | GAGGCGAGTA | GAGGCTGGTG | CGGAACTTGC | CGCCCCCAGC |
| 201 | AGCGCCGGCG | GGCTAAGCCC | AGGGCCGGGC | AGACAAAAGA |
| 241 | GGCCGCCCGC | GTAGGAAGGC | ACGGCCGGCG | GCGGCGGAGC |
| 281 | GCAGCGATGG | CCGGGCGAGG | GGGCAGCGCG | CTGCTGGCTC |

```
                M   A   G   R   G   G   S   A   L   L   A   L
321  TGTGCGGGGC ACTGGCTGCC TGCGGGTGGC TCCTGGGCGC
      C   G   A   L   A   A   C   G   W   L   G   A
361  CGAAGCCCAG GAGCCCGGGG CGCCCGCGGC GGGCATGAGG
      E   A   Q   E   P   G   A   P   A   A   G   M   R
401  CGGCGCCGGC GGCTGCAGCA AGAGGACGGC ATCTCCTTCG
      R   R   R   R   L   Q   Q   E   D   G   I   S   F   E
441  AGTACCACCG CTACCCCGAG CTGCGCGAGG CGCTCGTGTC
      Y   H   R   Y   P   E   L   R   E   A   L   V   S
481  CGTGTGGCTG CAGTGCACCG CCATCAGCAG GATTTACACG
      V   W   L   Q   C   T   A   I   S   R   I   Y   T
521  GTGGGGCGCA GCTTCGAGGG CCGGGAGCTC CTGGTCATCG
      V   G   R   S   F   E   G   R   E   L   L   V   I   E
561  AGCTGTCCGA CAACCCTGGC GTCCATGAGC CTGGTGAGCC
      L   S   D   N   P   G   V   H   E   P   G   E   P
601  TGAATTTAAA TACATTGGGA ATATGCATGG GAATGAGGCT
      E   F   K   Y   I   G   N   M   H   G   N   E   A
641  GTTGGACGAG AACTGCTCAT TTTCTTGGCC CAGTACCTAT
      V   G   R   E   L   L   I   F   L   A   Q   Y   L   C
```

*FIG. 1A.*

| | | | | |
|---|---|---|---|---|
| 681 | GCAACGAATA | CCAGAAGGGG | AACGAGACAA | TTGTCAACCT |
| | N E Y | Q K G | N E T | I V N L |
| 721 | GATCCACAGT | ACCCGCATTC | ACATCATGCC | TTCCCTGAAC |
| | I H S | T R I H | I M P | S L N |
| 761 | CCAGATGGCT | TTGAGAAGGC | AGCGTCTCAG | CCTGGTGAAC |
| | P D G F | E K A | A S Q | P G E L |
| 801 | TCAAGGACTG | GTTTGTGGGT | CGAAGCAATG | CCCAGGGAAT |
| | K D W | F V G | R S N A | Q G I |
| 841 | AGATCTGAAC | CGGAACTTTC | CAGACCTGGA | TAGGATAGTG |
| | D L N | R N F P | D L D | R I V |
| 881 | TACGTGAATG | AGAAAGAAGG | TGGTCCAAAT | AATCATCTGT |
| | Y V N E | K E G | G P N | N H L L |
| 921 | TGAAAAATAT | GAAGAAAATT | GTGGATCAAA | ACACAAAGCT |
| | K N M | K K I | V D Q N | T K L |
| 961 | TGCTCCTGAG | ACCAAGGCTG | TCATTCATTG | GATTATGGAT |
| | A P E | T K A V | I H W | I M D |
| 1001 | ATTCCTTTTG | TGCTTTCTGC | CAATCTCCAT | GGAGGAGACC |
| | I P F V | L S A | N L H | G G D L |
| 1041 | TTGTGGCCAA | TTATCCATAT | GATGAGACGC | GGAGTGGTAG |
| | V A N | Y P Y | D E T R | S G S |
| 1081 | TGCTCACGAA | TACAGCTCCT | CCCCAGATGA | CGCCATTTTC |
| | A H E | Y S S | S P D D | A I F |
| 1121 | CAAAGCTTGG | CCCGGGCATA | CTCTTCTTTC | AACCCGGCCA |
| | Q S L A | R A Y | S S F | N P A M |
| 1161 | TGTCTGACCC | CAATCGGCCA | CCATGTCGCA | AGAATGATGA |
| | S D P | N R P | P C R K | N D D |
| 1201 | TGACAGCAGC | TTTGTAGATG | GAACCACCAA | CGGTGGTGCT |
| | D S S | F V D G | T T N | G G A |
| 1241 | TGGTACAGCG | TACCTGGAGG | GATGCAAGAC | TTCAATTACC |
| | W Y S V | P G G | M Q D | F N Y L |
| 1281 | TTAGCAGCAA | CTGTTTTGAG | ATCACCGTGG | AGCTTAGCTG |
| | S S N | C F E | I T V | E L S C |
| 1321 | TGAGAAGTTC | CCACCTGAAG | AGACTCTGAA | GACCTACTGG |
| | E K F | P P E E | T L K | T Y W |

*FIG. 1B.*

| | | | | |
|---|---|---|---|---|
| 1361 | GAGGATAACA | AAAACTCCCT | CATTAGCTAC | CTTGAGCAGA |
| | E  D  N  K | N  S  L | I  S  Y | L  E  Q  I |
| 1401 | TACACCGAGG | AGTTAAAGGA | TTTGTCCGAG | ACCTTCAAGG |
| | H  R  G | V  K  G | F  V  R | D  L  Q  G |
| 1441 | TAACCCAATT | GCGAATGCCA | CCATCTCCGT | GGAAGGAATA |
| | N  P  I | A  N  A  T | I  S  V | E  G  I |
| 1481 | GACCACGATG | TTACATCCGC | AAAGGATGGT | GATTACTGGA |
| | D  H  D  V | T  S  A | K  D  G | D  Y  W  R |
| 1521 | GATTGCTTAT | ACCTGGAAAC | TATAAACTTA | CAGCCTCAGC |
| | L  L  I | P  G  N | Y  K  L  T | A  S  A |
| 1561 | TCCAGGCTAT | CTGGCAATAA | CAAAGAAAGT | GGCAGTTCCT |
| | P  G  Y | L  A  I  T | K  K  V | A  V  P |
| 1601 | TACAGCCCTG | CTGCTGGGGT | TGATTTTGAA | CTGGAGTCAT |
| | Y  S  P  A | A  G  V | D  F  E | L  E  S  F |
| 1641 | TTTCTGAAAG | GAAAGAAGAG | GAGAAGGAAG | AATTGATGGA |
| | S  E  R | K  E  E | E  K  E  E | L  M  E |
| 1681 | ATGGTGGAAA | ATGATGTCAG | AAACTTTAAA | TTTTTAAAAA |
| | W  W  K | M  M  S  E | T  L  N | F  . |
| 1721 | GGCTTCTAGT | TAGCTGCTTT | AAATCTATCT | ATATAATGTA |
| 1761 | GTATGATGTA | ATGTGGTCTT | TTTTTTAGAT | TTTGTGCAGT |
| 1801 | TAATACTTAA | CATTGATTTA | TTTTTTAATC | ATTTAAATAT |
| 1841 | TAATCAACTT | TCCTTAAAAT | AAATAGCCTC | TTAGGTAAAA |
| 1881 | ATATAAGAAC | TTGATATATT | TCATTCTCTT | ATATAGTATT |
| 1921 | CATTTTCCTA | CCTATATTAC | ACAAAAAAGT | ATAGAAAAGA |
| 1961 | TTTAAGTAAT | TTTGCCATCC | TAGGCTTAAA | TGCAATATTC |
| 2001 | CTGGTATTAT | TTACAATGCA | GAATTTTTTG | AGTAATTCTA |

FIG. 1C.

```
2041    GCTTTCAAAA ATTAGTGAAG TTCTTTTACT GTAATTGGTG

2081    ACAATGTCAC ATAATGAATG CTATTGAAAA GGTTAACAGA

2121    TACAGCTCGG AGTTGTGAGC ACTCTACTGC AAGACTTAAA

2161    TAGTTCAGTA TAAATTGTCG TTTTTTTCTT GTGCTGACTA

2201    ACTATAAGCA TGATCTTGTT AATGCATTTT TGATGGGAAG

2241    AAAAGGTACA TGTTTACAAA GAGGTTTTAT GAAAAGAATA

2281    AAAATTGACT TCTTGCTTGT ACATATAGGA GCAATACTAT

2321    TATATTATGT AGTCCGTTAA CACTACTTAA AAGTTTAGGG

2361    TTTTCTCTTG GTTGTAGAGT GGCCCAGAAT TGCATTCTGA

2401    ATGAATAAAG GTTAAAAAAA AATCCCCAGT GAAAAAAAA
```

```
                                        401                                                                                       480
gi/115892/sp/P16870/CBPH_HUMAN          G------------IDHDVTSAKDGDYWRLLIPGNYKLTASAPGYLAITK-----------KVAVP----YSPAAGVDFELESFSERKEEE
gi/115893/sp/P15087/CBPH_RAT_C          G------------IDHDVTSAKDGDYWRLLVPGNYKLTASAPGYLAITK-----------KVAVP----FSPAVGVDFELESFSERKEEE
gi/584896/sp/P37892/CBPH_LOPAM          G------------IDHDITTAKDGDYWRLLRQGNYKVAASAPGYLTVIK-----------KVAVP----HSPATRVDFELESLMERKEEE
gi/1750206_carboxypeptidase_E           SLATGFPIDHDIVSLEDGDYYRLLGNGYYHIQAKAEGFHPRSKCIRIENNIHVGVPSYDLRPATQMNFTLNPTKLPQESD
gi/3287958/sp/Q00493/CBPH_MOUS          G------------IDHDVTSAKDGDYWRLLAPGNYKLTASAPGYLAITK-----------KVAVP----FSPAVGVDFELESFSERKEEE
gi/1364188/gnl/PID/e153_CPE_a           G------------IDHDVTSAKDGDYWRLLVPGNYKLTASAPGYLAIAK-----------KVAVP----YSPAVRVDFELESFSERKEEE
                                        481                                                                                       560
gi/115892/sp/P16870/CBPH_HUMAN          KEE------LMEWWKMSETLNF---------------------------------------------------------
gi/115893/sp/P15087/CBPH_RAT_C          KEE------LMEWWKMSETLNF---------------------------------------------------------
gi/584896/sp/P37892/CBPH_LOPAM          REE------LMDWWKMSETLNF---------------------------------------------------------
gi/1750206_carboxypeptidase_E           KKEDYNCERLWNEVQMETQLEDRELLVSVLSYLQPQTKWSLLADQLSTLELYSLLAEALKELNPDQMREVLERLPHAVQE
gi/3287958/sp/Q00493/CBPH_MOUS          KEE------LMEWWKMSETLNF---------------------------------------------------------
gi/1364188/gnl/PID/e153_CPE_a           KEE------LMEWWKMSETLNF---------------------------------------------------------
                                        561            572
gi/115892/sp/P16870/CBPH_HUMAN          -------------------------------------------------------------------------------
gi/115893/sp/P15087/CBPH_RAT_C          -------------------------------------------------------------------------------
gi/584896/sp/P37892/CBPH_LOPAM          -------------------------------------------------------------------------------
gi/1750206_carboxypeptidase_E           QLELVISAHMSK
gi/3287958/sp/Q00493/CBPH_MOUS          -------------------------------------------------------------------------------
gi/1364188/gnl/PID/e153_CPE_a           -------------------------------------------------------------------------------
```

*FIG. 2B.*

```
gi/115892/sp/P16870/CBPH_HUMAN      1                                                                                  80
gi/115894/sp/P14384/CBPM_HUMAN      ~~~~~~~~~~~~~~~~~~~~~~~~~~~~~~~~~~~~~~~~~~~~~~~~~~~~~~~~~~~~~~~~~~~~~~~~~~~~~MAG
gi/30297_carboxypeptidase_N_pr      ~~~~~~~~~~~~~~~~~~~~~~~~~~~~~~~~~~~~~~~~~~~~~~~~~~~~~~~~~~~~~~~~~~~~~~~~~~~~~~~~
gi/2160714_carboxypeptidase_z_      MPPPPLLLLTLVLVVAAARPGCEFERNPAATCVDLQLRTCSDAAYNHTFPNLLQHRSWEVVEASSEYILLSVLHQLLEG gi/115892/sp/P16870/CBPH_HUMAN                                                                                       160
gi/115894/sp/P14384/CBPM_HUMAN      RGGSALIAL-CGALAA-C--GWLLG--------AEAQEPGAPAAGMRR-------RRRLQQED---------G------
gi/30297_carboxypeptidase_N_pr      ~~~~~~~~~~~~~~~~~~~~~~~~~~~~~~~~~~~~~~~~~~~~~~~~~~~~~GIWL------GLLLPLVAA------
gi/2160714_carboxypeptidase_z_      QCNPDLRLLGCAVLAPRCEGGWVRRPCRHICEGLREVCQPAFDAIDMAWPYFLDCHRYFTREDEGCYDPLEKLRGLEAD gi/115892/sp/P16870/CBPH_HUMAN      161                                                                              240
gi/115894/sp/P14384/CBPM_HUMAN      -------ISFEYHRYPELREALVSWLQCTAISRIYTVGRSFEGRELLVIELSDNPGVHEPGEPEFKYIGMHGNE
gi/30297_carboxypeptidase_N_pr      -------LDFNYHRQEGMEAFLKTVAQNYXXVTHLHSIGKSVKGRNLWLVVGRFPKEHRIGIPEFKYVANMHGDE
gi/2160714_carboxypeptidase_z_      -------VTFRHHRYDDLVRTLYKVQNECPGITRVYSIGRSVEGRHLYVLEFSDHPGIHEPLEPEVKYVGNMHG
                                    EALPSGLPPTFIRFSHHSYAQMVRVLRRTASRCAHVARTYSIGRSFDGRELLVIEFSSRPGQHELMEPEVKLIGNIHGNE gi/115892/sp/P16870/CBPH_HUMAN      241                                                                              320
gi/115894/sp/P14384/CBPM_HUMAN      AVGRELLIFLAQYLCNEYQKGNETIVNLIHSTRIHIMPSLNPDGFEKAASQPGELKDWFVGRSNAQGIDLNRNFPDLDRI
gi/30297_carboxypeptidase_N_pr      TVGRELLLHLIDYLVTSDGK-DPEITNLINSTRIHIMPSMNPDGFEAVK-KPD--CYYSIGRENYNQYDLNRNFPDAFEY
gi/2160714_carboxypeptidase_z_      NEALGREIMLQLSEFLCEEFRNRNQRIVQLIQDTRIHILPSMNPDGYEVAAAQGPNKPGYLVGRNNANGVDLNRNFPDLN
                                    VAGREMLIYLAQYLCSEYLLGNPRIQRLLNTTRIHLLPSINPDGYEVAAAEGAGYNGWTSGRQNAQNLDLNRNFPDLTSE gi/115892/sp/P16870/CBPH_HUMAN      321                                                                              400
gi/115894/sp/P14384/CBPM_HUMAN      VY-VNEKEGGPNNHLLKNMKKIVDQNTKLAPETKAVIHWIMDIPFVLSANLHGGDLVANYPYDETRSGS------AHEYSS
gi/30297_carboxypeptidase_N_pr      NN------VSRQ-----------------PE--TVAVMKWLKTETFVLSANLHGAIVASYPFDNGVQATG---ALYSRSL
gi/2160714_carboxypeptidase_z_      TYIY-YNEKYGGPNHHLPLPDNWKSQ-----VEPETRAVIRMHSFNFVLSANLHGGAVVANYPDKSFEHRVGVRRTAS
                                    YYRLAETRGARSDHIPIPQHYWWG------KVAPETKAIMKWMQTIPFVLSASLHGGDLVVSYPFDFSKHPQE----EKMFSP gi/115892/sp/P16870/CBPH_HUMAN      401                                                                              480
gi/115894/sp/P14384/CBPM_HUMAN      SPDDAIFQSLARAYSSFNPAMSDPNRPPCRKNDDDSSFVDG-TTNGGAWYSVPGGMQDFNYLSSNCFEITVELSCEKFPP
gi/30297_carboxypeptidase_N_pr      TPDDDVFQYLAHTYASRNPNMKKG--DECKNKMN----FPNG-VTNGYSWYPLQGGMQDYNYIWAQCFEITLELSCCKYPR
gi/2160714_carboxypeptidase_z_      TPTPDDKLFQKLAKVYSYAHGWMFQG--WNCGDY------FPDG-ITNGASWYSLSKGMQDFNYLHTNCFEITELSCDKF
                                    TPDEKRMFKLLSRAYADVHPMMDRSENRCGGN-----FLKRGSIINGADWYSFTGGMSDFNYLHTNCFEITVELGCVKFPP
                                              ↑POSITIVELY CHARGED gi/115892/sp/P16870/CBPH_HUMAN      481                                                                              560
gi/115894/sp/P14384/CBPM_HUMAN      EETLKTYWEDNKNSLLISYLEQIHRGVKGFVRDLQGNPIANATISVEGIDH--DVTSAKDGDYWRLLIPGNYKLTASAPGY
gi/30297_carboxypeptidase_N_pr      EEKLPSFWNNNKASLLEYIKQVHLGVKGQVFDQNGNPLPNVIVEVQDRKHICPYRTNKYGEYLLLLPGSYINVTVPGH
gi/2160714_carboxypeptidase_z_      PPEEELQREWLGNREALIQFLEQVHQGIKGMVLDENYNNLANAVISVSGINH--DVTSGDHGDYFRLLPGIYTVSATAP
                                    EEALYTLWQHNKESLLNFVETVHRGIKGVVTDKFGKPVKNARISVKGIRH--DITTAPDGDYWRLLPPGIHIVIAQAPGY
```

FIG. 3A.

```
                                      561                                                                                       640
gi/115892/sp/P16870/CBPH_HUMAN        LAITKKVAVP---YSPAAGVDFELESF------------------------------SE-------RXEEEKEELMEWWKRMM
gi/115894/sp/P14384/CBPM_HUMAN        DPHITKVIIPEKSQNFSALKDILLPFQG-------------------------QLDSIPVSNPSCPMIPLYRNLPDHSAATKPSLFLF
gi/30297_carboxypeptidase_N_pr        GYDPETVTVTG---PAEPTLVNFHLKRS------------------------IPQVSPVRRAPSRRHGVRAKVQPQAR
gi/2160714_carboxypeptidase_z         AKVIKKVIIPAR-MKRAGRVDFILQPLGMGPKNFIHGLRRTGPHDPLGGASSLGEATEPDPLRARRQPSADGSKPWWWSY 641                 657
gi/115892/sp/P16870/CBPH_HUMAN        SETLNF------
gi/115894/sp/P14384/CBPM_HUMAN        LVSLLHIFFK-----
gi/30297_carboxypeptidase_N_pr        KKEMEMRQLQRGPA---
gi/2160714_carboxypeptidase_z         FTSLSTHRPRWLLKY
```

FIG. 3B.

METHOD OF DETECTING RISK OF TYPE II DIABETES BASED ON MUTATIONS FOUND IN CARBOXYPEPTIDASE E

RELATED APPLICATION

This application claims the benefit of U.S. Provisional application Ser. No. 60/105,102, filed Oct. 21, 1998.

FIELD OF THE INVENTION

The invention is directed to methods for diagnosing Type II diabetes or the risk for developing Type II diabetes by detecting alterations in expression, sequence, or function of carboxypeptidase E nucleic acid or protein. The invention is also directed to methods for preventing or treating Type II diabetes by modulating the levels, altering the sequence, or controlling the function of carboxypeptidase E nucleic acid or protein. The invention is also directed to methods for identifying agents that modulate the levels or affect the function of carboxypeptidase E nucleic acid or protein. The invention is also directed to methods using the agents to treat or diagnose Type II diabetes. The invention is also directed to animal models of Type II diabetes using the carboxypeptidase E gene. The invention is also directed to compositions based on carboxypeptidase E nucleic acid or protein useful for treating or diagnosing diabetes, identifying compounds for treating or diagnosing diabetes, and developing models of diabetes.

BACKGROUND OF THE INVENTION

Carboxypeptidase E

Carboxypeptidase E (CPE), known also as carboxypeptidase H and enkephalin convertase, is involved in the processing of various bioactive peptides including peptide hormones and neurotransmitters (Fricker, in *Peptide Biosynthesis and Processing*) Fricker, ed. (pages 199–230 CRC Press, Boca Raton, Fla.) (1991). Many peptide hormones and neurotransmitters are initially produced as precursors that are enzymatically processed into bioactive peptides (Fricker *J. Cell Biochem.* 38:279–289 (1988)). Initially, endopeptidases cleave the prohormone precursor at multiple basic amino acid cleavage sites (Varlamov et al. *J. Biochem.* 271:13981–13986 (1996)). Then a carboxypeptidase removes the basic amino acids from the C terminus of the peptide to generate either the bioactive product or a precursor to form the C-terminal amide group. This process is important for the production of bioactive peptides in many tissues.

CPE is present in many tissues where peptide biosynthesis occurs including brain, pituitary, and adrenal medulla (Fricker, *J. Cell. Biochem.*, cited above). The activity is localized to secretory granules where CPE exists in membrane and soluble forms (Manser et al. *Biochem. J.* 267:517–525 (1990)). CPE does not appear to contain a transmembrane-spanning helical region, which suggests that CPE is membrane bound through another mechanism. A recent study has shown that the C-terminal region of CPE particularly the C-terminal 14 amino acids are required for membrane binding (Varlamov et al. *J. Biol. Chem.* 271:6077–6083 (1996)). Using deletion mutation and fusion protein analysis to study membrane binding and targeting, the authors concluded that there were three separate functions within the C-terminal region of CPE. The 51 C-terminal amino acids appear to direct the sorting to the membrane. Another important region, located 23–33 amino acids from the C-terminus appear to be required for proper folding in that protein lacking this region is neither active nor secreted. A third domain, located within the predicted amphiphilic helix of the C-terminal 14 residues was involved with a binding of CPE to membranes.

A high degree of conservation of the C-terminal region among CPE from different species has been shown. The last exon which encodes the C-terminal 32 amino acids is a hundred percent identical in human, rat, mouse, and bovine CPE and contains only 4 conservative substitutions in angler fish CPE (Varlamov, *J. Biochem.* 271, cited above).

Within secretory granules, CPE has been shown to be present in several forms having different solubility. Different forms of CPE have been purified to apparent homogeneity (Supattapone et al. *J. Neurochem.* 42:1017 1984); and (Fricker et al. *J Biol. Chem.* 258:10950 (1983)). Soluble and membrane associated forms have similar enzymatic and physical properties (Pricker, *J. Cell. Biochem.*, cited above). Both forms have the same amino acid sequence at the N-terminal region (Fricker et al. *Nature* 323:461 (1986)). It has thus been suggested that differences between soluble and membrane forms may be the result of post-translational modifications of a single precursor protein (Fricker *J. Cell. Biochem.*, cited above). It has been shown that membrane and soluble forms of CPE are synthesized in the rough endoplasmic reticulum and apparently derived from a single mRNA species by post-translational processing. Synthesis of translation products from human CPE mRNA in a reticulocyte lysate in the presence of microsomal membranes produced 3 processed forms of CPE also showing differences in glycosylation (Manser et al., cited above).

Non-insulin-dependent diabetes mellitus

Diabetes mellitus is among the most common of all metabolic disorders, affecting up to 11% of the population by age 70. Type I diabetes (insulin-dependent diabetes mellitus or IDDM) represents about 5 to 10% of this group and is the result of progressive autoimmune destruction of the pancreatic β-cells with subsequent insulin deficiency.

Type II diabetes (non-insulin dependent diabetes mellitus, or type II diabetes) represents 90–95% of the affected population, more than 100 million people worldwide (King et al. (1988) *Wld. Hlth. Statist. Quart.* 41:190–196; Harris et al. (1992) *Diabetes Care* 15:815–819), and is associated with peripheral insulin resistance, elevated hepatic glucose production, and inappropriate insulin secretion (DeFronzo, R. A. (1988) *Diabetes* 37:667–687). Family studies point to a major genetic component (Newman et al. (1987) *Diabetologia* 30:763–768; Kobberling, J. (1971) *Diabetologia* 7:46–49; Cook, J. T. E. (1994) *Diabetologia* 37:1231–1240). However, few susceptibility genes have been identified.

Familial predisposition for obesity is the major phenotypic risk factor associated with development of type II diabetes in humans. This obesity is usually accompanied by the development of insulin resistance (Naggert et al. *Nature: Genetics* 10:135–141 (1995)).

In mice, six different loci on five different chromosomes produce the obesity-diabetes syndrome. These mutations affect not only obesity and insulin resistance but also other neuroendocrine disturbances. One of these mutations (fat/fat) is associated with a lesion in the CPE gene. The fat mutation maps to mouse chromosome 8 close to the gene for CPE. It was first shown that in extracts of fat/fat pancreatic islets and pituitaries, proinsulin processing was severely reduced. This was associated with a ser202pro mutation in the CPE coding region. This mutation was shown to abolish enzymatic activity in vitro. Thus, this mutation was proposed to demonstrate an obesity-diabetes syndrome caused by a defect in a prohormone processing pathway, i.e., in CPE (Naggert et al. cited above). The importance of this mutation in CPE function in mice was further investigated by studying the effects on activity, amount, and properties of CPE with ser to pro, ala, gly, or phe substitutions at amino acid 202. In an in vitro system, phe and pro mutants were enzymatically inactive, could not bind to a substrate, and were not secreted. Ala or gly mutants, however, exhibited normal enzymatic activities. In a mouse pituitary derived cell line, pro and phe mutants were not secreted. Further, they were degraded within several hours. The analysis of CPE from pituitary cells derived from fat/fat mice showed that the natural pro mutant produced in these cells was not secreted but was degraded. These results provided further support for the hypothesis that fat/fat mice are defective in CPE activity because of the ser to pro substitution at amino acid 202. A subsequent study examined CPE activity and peptide processing in several tissues of fat/fat mice. The report found that there is no active CPE in these mice. It was concluded therefore that the ser to pro mutation causes the enzyme to be completely inactive. It was also concluded that the absence of active CPE causes a large decrease in the levels of fully processed peptides, such as the enkephalins (Fricker et al. *J. Biol. Chem.* 271:30619–30624 (1996)). These results were consistent with those found for proinsulin and proneurotensin in the fat/fat mouse. Accordingly, the reference concluded that a deficiency of CPE in the fat/fat mouse leads to a dramatic accumulation of peptides with C-terminal basic residues, and a decrease in the levels of correctly processed peptides. Although the authors proposed several mechanisms by which CPE acts on prohormones (for example, by being required for endopeptidase activity), the actual mechanism was not elucidated.

A recent report addressed the question of whether proinsulin targeting to secretory granules is impaired in fat/fat mice. The report showed that CPE is not essential for sorting of proinsulin to these granules (Irminger et al. *J. Biol. Chem.* 272:27532–27534 (1997)).

Although defects in loci encoding proinsulin conversion enzymes have been postulated as a mechanism for producing hyperproinsulinaemia in humans, clinical cases demonstrating genetic defects in this pathway in humans have not appeared definitively in the literature. One report cited a severely obese Caucasian female patient who exhibited a possible defect in the prohormone convertase 1-catalyzed conversion of proinsulin (Naggert et al., cited above).

Recently, the question of whether CPE plays a role in the pathogenesis of type II diabetes in humans was addressed (Utsunomiya, et al. *Diabetologia* 41:701–705 (1998)). Insulin is synthesized in the pancreatic P cell as a prohormone that is converted to insulin and C-peptide by the action of prohormone convertase II, prohormone convertase III, and CPE. In type II diabetes, the proinsulin level and/or proinsulin: insulin ratio is increased. It was thus considered that mutations in these enzymes could contribute to the development of type II diabetes. Further, the identification of a mutation in a CPE gene of the fat/fat mouse that is associated with hyperproinsulinemia and late onset obesity- diabetes suggested the possibility that a mutation in CPE might be involved in the development of these syndromes in humans. Thus, the CPE gene was screened for mutations in a group of human subjects with type II diabetes and obesity. 269 subjects with type II diabetes, 28 non-diabetic obese subjects, and 104 non-obese and non-diabetic controls were studied. No correlation could be made between a CPE gene nucleotide substitution and type II diabetes or obesity. The authors noted that although the relationship between the loss of CPE activity and obesity-diabetes was not clear, the loss of CPE activity did cause defects in the processing of prohormone neuropeptides associated with controlling satiety. However, the authors concluded that none of the nucleotide substitutions were associated with NIDDM or obesity and that genetic variation in the CPE gene does not appear to play a major role in the pathogenesis of NIDDM or obesity in humans.

Accordingly, there is still a need to identify genetic factors that are important in developing type II diabetes. It is specifically important to determine if the CPE gene could be useful for treating or diagnosing type II diabetes in humans.

SUMMARY OF THE INVENTION

A general object of the invention is to identify polynucleotides and polypeptides associated with the development of or risk for developing Type II diabetes.

A further general object of the invention is to use these polypeptides and polynucleotides for treatment or diagnosis of Type II diabetes.

A further general object of the invention is to use these polypeptides and polynucleotides to identify compounds modulating the expression or function of the polypeptides or polynucleotides.

A further general object of the invention is to use these compounds to modulate or otherwise interact with the polypeptides and polynucleotides associated with Type II diabetes for the treatment and diagnosis of the disorder.

A more specific object of the invention is to exploit the relationship between altered levels of expression or mutation in the CPE gene and the development of or risk of developing type II diabetes in humans. Thus, it is a further specific object of the invention to use CPE polypeptides and polynucleotides for treatment and diagnosis of type II diabetes and for identifying compounds that can modulate expression or function of the polypeptides or polynucleotides and are thus useful for treatment and diagnosis of type II diabetes.

The invention is based on the inventors' discovery that mutations in the carboxypeptidase E gene correlate with Type II diabetes in humans.

Accordingly, the invention is directed to CPE polynucleotides and polypeptides that are associated with the development of or risk for developing Type II diabetes. In a specific disclosed embodiment, the invention encompasses a coding mutation, arg→trp 283, corresponding to a c→t nucleotide change at this position.

The invention is also directed to using CPE polypeptides and polynucleotides for treatment and diagnosis of Type II diabetes. The polypeptides and polynucleotides serve as both targets and reagents for treatment and diagnosis.

The invention is also directed to using the polynucleotides and polypeptides to identify compounds that are useful in the treatment and diagnosis of Type II diabetes. The compounds can act as agonists or antagonists of CPE expression or function. The polynucleotides and polypeptides serve as both a target to identify compounds and may themselves provide a source for derivative compounds that can act as an agonist or antagonist of CPE expression or function.

The invention is further directed to using these compounds to treat and diagnose Type II diabetes.

Specifically, the invention is directed to methods for detecting an abnormal level of the CPE gene or gene product, a mutation in the gene or gene product, or otherwise abnormal gene or gene product, in cells or tissues of individuals having type II diabetes or the risk of developing type II diabetes or in cell or animal models of the disorders.

The invention is thus directed to methods for screening for Type II diabetes or the risk of developing Type II diabetes by detecting the CPE gene or gene product. Abnormal levels, mutation, or other abnormality allows the diagnosis of Type II diabetes or risk of developing Type II diabetes. In one embodiment, the invention is directed to monitoring treatment outcome in a patient, in clinical trials, or in animal models, by detecting the CPE gene or gene product for abnormal levels, mutation, or other abnormality.

The invention is thus also directed to methods for treating individuals with type II diabetes, or the risk of developing type II diabetes, using the abnormal levels, mutation, or other abnormality in the CPE gene or gene product as a reagent or target for treatment. In one embodiment, methods are directed to treating cells, tissues, or animal models associated with the disorder using the CPE gene or gene product as a reagent or target for treatment.

The invention is thus also directed to methods using the CPE gene or gene product as a reagent or target to screen for agents that modulate the levels or effectively reverse the mutation or other abnormality in the CPE gene or gene product. Accordingly, the invention provides methods for identifying agonists and antagonists of the CPE gene or gene product. These agents can be used to diagnose or treat Type II diabetes by their effects on the level or function of the CPE gene or gene product. By identifying agents that are capable of modulating the expression or function of the CPE gene or gene product, methods are thus provided for affecting the development of or course of Type II diabetes in an individual by modulating the level or function of the CPE gene or gene product. Further, by providing these agents that modulate the expression, methods are provided for assessing the effect of treatment in cell and animal models.

By identifying agents that are capable of interacting with, or otherwise allowing detection of abnormal expression or function of the CPE gene or gene product, methods are thus provided for diagnosing the development of, or risk of developing, type II diabetes. This can be in the context of an individual patient, monitoring clinical trials, and assessing CPE gene function or efficacy of treatment in cell and animal models.

The invention further encompasses compositions based on the CPE gene or gene product that are useful for detection or modulation of the expression or function of the CPE gene or gene product. Thus, these compositions are useful for the diagnosis or treatment of Type II diabetes.

The invention also provides cell and animal model systems for studying Type II diabetes based on alterations in the CPE gene or gene product in the model.

In one embodiment, the polynucleotides and polypeptides useful in the compositions and methods described herein contain a mutation in the coding region, arg→trp 283, corresponding to a c→t nucleotide change at this position. However, any CPE variant that is associated with type II diabetes is useful for the compositions and methods described herein. Further, as described below, wild-type CPE gene or gene product can be useful as a target for treatment and diagnosis in instances in which an alteration in CPE that correlates with type II diabetes does not reside in the presence of a nucleotide or amino acid mutation.

DESCRIPTION OF THE DRAWINGS

FIG. 1 shows the human carboxypeptidase E amino acid SEQ ID NO:2 and nucleotide sequence SEQ ID NO:1 identifying the amino acid change from arginine to tryptophan in all members of the family at amino acid 283. This corresponds to a C→T nucleotide change at this position.

Figure 2A:
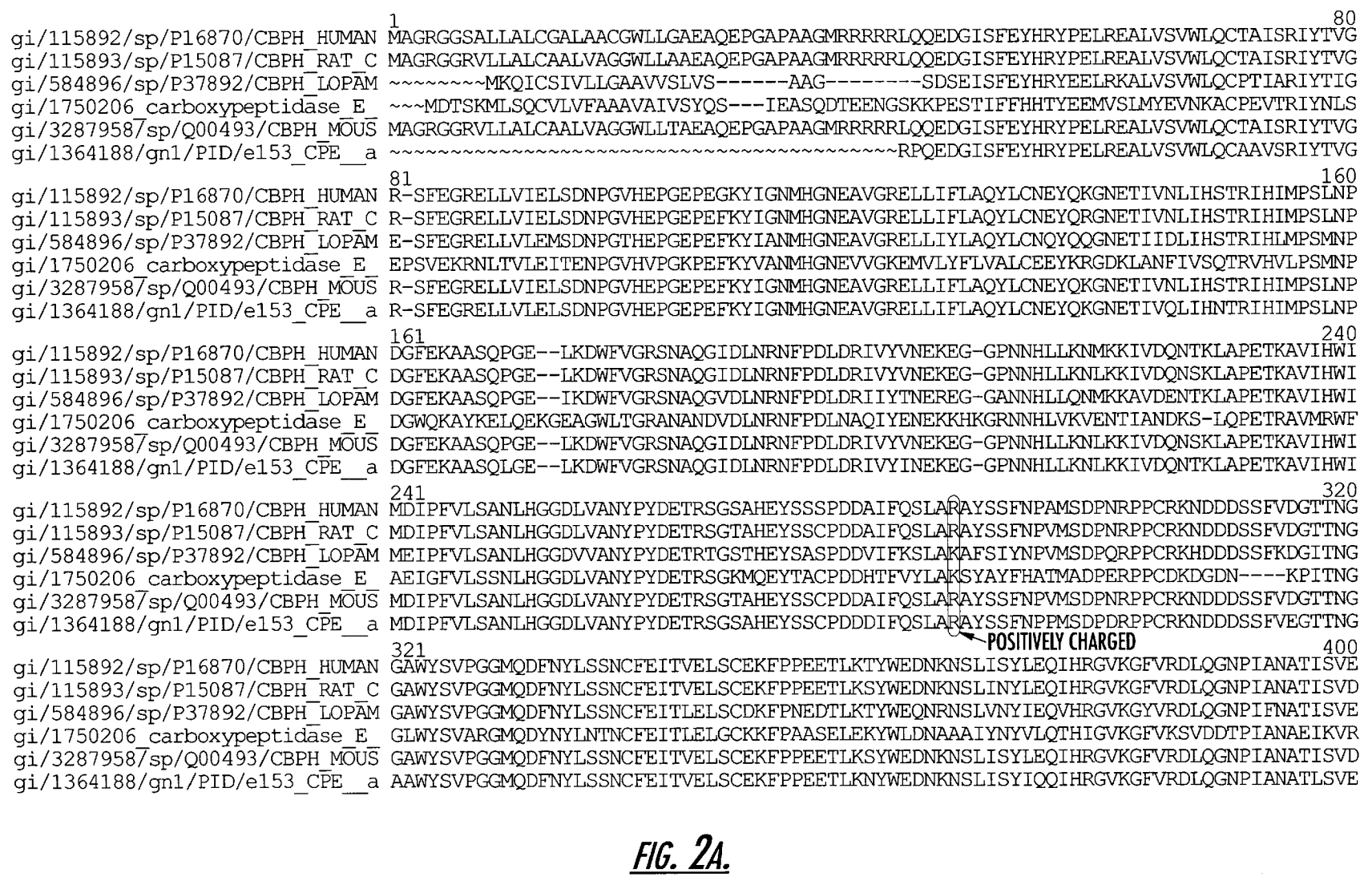

FIG. 2 shows an alignment of carboxypeptidase E from various species (from top to bottom: human SEQ ID NO:2, rat SEQ ID NO:3, lopam SEQ ID NO:4, bovine SEQ ID NO:5, murine SEQ ID NO:6, and alysia SEQ ID NO:7).

FIG. 3 shows an alignment of carboxypeptidase homologs (CPE SEQ ID NO:2, CPM SEQ ID NO:8, CPN SEQ ID NO:9, and CPZ SEQ ID NO:10).

DETAILED DESCRIPTION OF THE INVENTION

The inventors have discovered that expression of an altered form of carboxypeptidase E is a factor in Type II diabetes in humans. Specifically, the inventors have discovered the occurrence of a specific mutation in the carboxypeptidase E gene in two families with the Type II diabetes phenotype. In an initial screening of approximately 20 Type II diabetes individuals against 20 controls for mutations in the carboxypeptidase E gene, the inventors identified a coding mutation (ARG→TRP 283) in an affected individual (FIG. 1). Two affected siblings were then screened and also found to have the mutation. In this family, all three affected siblings were heterozygous for the mutation.

Subsequent to this study, the mutation was further identified in 3 unrelated affected families. In the first family, three siblings were studied. The two affected siblings were found to contain the mutation. The mutation was lacking in the third, non-affected sibling. In the second affected pedigree, two of the four siblings contained the mutation, while the other two did not. The two with the mutation appeared to be most significantly affected, judged by the age of onset. In the third affected family, only one of the two affected siblings had this mutation. All affected patients were heterozygous for the mutation. These studies link misexpression of the carboxypeptidase E gene to type II diabetes in humans (but not obesity).

The invention is therefore directed to methods using the CPE gene or gene product as a target to detect Type II diabetes or the risk of developing Type H diabetes. The invention is also directed to methods for determining the molecular basis for type II diabetes or the risk of developing type II diabetes using the CPE gene or gene product as a target.

It is understood that "gene product" refers to all molecules derived from the gene, especially RNA and protein. cDNA is also encompassed, where, for example, made by naturally-occurring reverse transcriptase.

In one embodiment, the gene itself is detected. Alterations in copy number, genomic position, and nucleotide sequence can be detected. Alterations in nucleotide sequence include insertion, deletion, point mutation, and inversion. One or more alterations in sequence can occur at any position within the gene, including coding, noncoding, transcribed, and non-transcribed, regulatory regions. Other alterations that can be detected include nucleic acid modification, such as methylation, gross rearrangement in the genome such as in a homogeneously-staining region, double minute chromosome or other extrachromosomal element, or cytoskeletal arrangement.

The invention also encompasses the detection of RNA transcribed from the CPE gene. Detection encompasses alterations in copy number and nucleotide sequence. Sequence changes include insertion, deletion, point mutation, inversion, and splicing variation. Detection of CPE RNA can be indirectly accomplished by means of its cDNA.

CPE DNA and RNA levels and gross rearrangement can be analyzed by any of the standard methods known in the art.

Nucleic acid can be isolated from the cell or analyzed in situ in a cell or tissue sample. For detecting alterations in nucleic acid levels or gross rearrangement, all, or any part, of the nucleic acid molecule can be detected. Nucleic acid reagents derived from any desired region of the CPE gene can be used as a probe or primer for these procedures. Copy number can be assessed by in situ hybridization or isolation of nucleic acid from the cell and quantitation by standard hybridization procedures such as Southern or Northern analysis. Genes can be amplified in the forms of homogeneously-staining regions or double minute chromosomes. Accordingly, one method of detection involves assessing the cellular position of an amplified gene. This method encompasses standard in situ hybridization methods, or alternatively, detection of an amplified fragment derived from digestion with an appropriate restriction enzyme recognizing a sequence that is repeated in the amplified unit.

Identifying nucleic acid modifications, such as methylation, can be analyzed by any of the known methods in the art for digesting nucleic acid and analyzing modified nucleotides, such as by BPLC, thin-layer chromatography, mass spectra analysis, and the like.

Gross rearrangements in the genome are preferably detected by means of in situ hybridization, although this type of alteration can also be assessed by means of assays involving normal cellular components with which the genes are normally found, such as in specific membrane preparations.

Mutations in CPE nucleic acid can be analyzed by any of the standard methods known in the art. Nucleic acid can be isolated from a cell or analyzed in situ in a cell or tissue sample by means of specific hybridization probes designed to allow detection of the mutation. In this embodiment, the portion of the nucleic acid that is detected preferably contains the mutation. However, it is understood that in some embodiments, as where the mutation affects secondary structure or other cellular association, distant regions affected by the mutation can be detected. In this embodiment, nucleic acid reagents are preferably derived from the mutated region of the CPE gene to be used as a probe or primer for the procedures. However, as discussed above, nucleic acid reagents useful as probes can be derived from any position in the nucleic acid. RNA or cDNA can be used in the same way.

In certain embodiments, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a CPE gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site.

Perfectly matched sequences can be distinguished from mismatched sequences by nuclease cleavage digestion assays or by differences in melting temperature.

Sequence changes at specific locations can also be assessed by nuclease protection assays such as RNase and SI protection or the chemical cleavage method.

Furthermore, sequence differences between a mutant CPE gene and a wild-type gene can be determined by direct DNA sequencing. A variety of automated sequencing procedures can be utilized when performing the diagnostic assays ((1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include, selective oligonucleotide hybridization, selective amplification, and selective primer extension.

Methods of detection also encompass detection of the CPE protein. Detection encompasses assessing protein levels, mutation, post-translational modification, and subcellular localization. Mutations encompass deletion, insertion, substitution and inversion. Mutations at RNA splice junctions can result in protein splice variants.

CPE protein levels can be analyzed by any of the standard methods known in the art. Protein can be isolated from the cell or analyzed in situ in a cell or tissue sample. Quantitation can be accomplished in situ, for example by standard of fluorescence detection procedures involving a fluorescently labeled binding partner such as an antibody or other protein with which the CPE protein will bind. This could include a substrate upon which the protein acts or an enzyme which normally acts on the protein. Quantitation of isolated protein can be accomplished by other standard methods for isolated protein, such as in situ gel detection, Western blot, or quantitative protein blot. Levels can also be assayed by functional means, such as the effects upon a specific substrate. In the case of the CPE protein, this could involve cleavage of basic amino acids from the C terminus of the various peptide substrates upon which the CPE protein normally acts, or artificial substrates designed for this assay. It is understood that any enzyme activity contained in the CPE protein can be used to assess protein levels.

Mutations in CPE protein can be analyzed by any of the above or other standard methods known in the art. Protein can be isolated from the cell or analyzed in situ in a cell or tissue sample. Analytic methods include assays for altered electrophoretic mobility, binding properties, tryptic peptide digest, molecular weight, antibody-binding pattern, isoelectric point, amino acid sequence, and any other of the known assay techniques useful for detecting mutations in a protein. Assays include, but are not limited to, those discussed in Varlamov et al., *J. Biol. Chem.* 271:13981 (1996), incorporated herein by reference for teaching such assays. These include C-terminal arginine binding, acidic pH optima, sensitivity to inhibitors, thermal stability, intracellular distribution, endopeptidase activity, effect on endopeptidase inhibitor, substrate affinity, enzyme kinetics, membrane association, posttranslational modification, active site confirmation, compartmentalization, binding to substrate, secretion, and turnover. Further assays for function can be found in Fricker, *J. Cell Biochem.* 38:279–289 (1988), and Manser et al., *Biochem. J.* 267:517–525, (1990), both incorporated by reference for teaching specific functions that can be assayed for mutation in the CPE gene.

In vitro techniques for detection of the protein include enzyme linked immunosorbent assays (ELISAs), Western blots, immunoprecipitations and immunofluorescence. Alternatively, the protein can be detected in vivo in a subject by introducing into the subject a labeled anti-CPE antibody. For example, the antibody can be labeled with a radioactive marker whose presence and location in a subject can be detected by standard imaging techniques. For detection of specific mutation in the protein, antibodies, or other binding partners, can be used that specifically recognize these alterations. Alternatively, mutations can be detected by direct sequencing of the protein.

Other alterations that can be detected include alterations in post-translational modification. Amino acids, including the terminal amino acids, may be modified by natural processes, such as processing and other post-translational modifications. Common modifications that occur naturally in polypeptides are described in basic texts, detailed monographs, and the research literature, and they are well known to those of skill in the art.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well-known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of Proteins,* B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

In addition to detection methods that involve specific physical features, functional characteristics of the protein are also useful for detection with known methods. These include changes in biochemistry, such as substrate affinity, enzyme kinetics, membrane association, active site conformation, compartmentalization, forming a complex with substrates or enzymes that act upon the protein, secretion, turnover, pH optima, sensitivity to inhibitors, thermal stability, endopeptidase activity, effects on endopeptidase inhibitors, and any other such functional characteristic that is indicative of a mutation or alteration in post-translational modification. Specific assays can be found in the literature (e.g., see Varlamov et al. (1996) *J. Biol. Chem.* 271:13981).

CPE gene and gene product can be detected in a variety of systems. These include cell-free and cell-based systems in vitro, tissues, such as ex vivo tissues for returning to a patient, in a biopsy, and in vivo, such as in patients being treated, for monitoring clinical trials, and in animal models. Cell-free systems can be derived from cell lines or cell strains in vitro, including recombinant cells, cells derived from patients, subjects involved in clinical trials, and animal models, including transgenic animal models. In one embodiment, CPE gene and gene product can also be detected in cell-based systems. This includes cell lines and cell strains in vitro, including recombinant lines and strains containing the CPE gene, explanted cells such as primary cultures, particularly those derived from a patient with type II diabetes, subjects undergoing clinical trials, and animal models of diabetes including transgenic animals. The CPE gene and gene product can also be detected in tissues. These include tissues derived from patients with type II diabetes, subjects undergoing clinical trials, and animal models. In one embodiment, the tissues are those affected in type II diabetes. CPE gene and gene product can also be detected in individual patients with type II diabetes, and subjects undergoing clinical trials, and in animal models of diabetes, including transgenic models. Preferred sources of detection include cell and tissue biopsies from individuals affected with diabetes or at risk for developing diabetes.

In addition to detecting the CPE gene or gene product directly, the invention also encompasses the use of compounds that produce a specific effect on a variant CPE gene or gene product as a further means of diagnosis. This includes, for example, detection of binding partners, including binding partners specific for variant CPE genes or gene products, and compounds that have a detectable effect on a function of CPE genes or gene products. For example, an increase in CPE levels can be detected by a complex formed between the CPE and a binding partner or levels of free CPE binding partner. As a further example, abnormally high CPE activity could be detected by concurrently high amounts of CPE processed substrate.

All these methods of detection can be used in procedures to screen individuals at risk for developing or having Type II diabetes. Further, detection of the alterations of the gene or gene products in individuals can serve as a prognostic marker for developing diabetes or diagnostic marker for having diabetes when the individuals are not known to have diabetes or to be at risk for having diabetes.

Diagnostic assays can be performed in cell-based systems, and particularly in cells associated with type II diabetes, in intact tissue, such as a biopsy, and nonhuman animals and humans in vivo. Diagnosis can be at the level of nucleic acid or polypeptide.

The invention also encompasses methods for modulating the level or activity of CPE gene or gene product.

At the level of the gene, known recombinant techniques can be used to alter the gene in vitro or in situ. Excessive copies of, or all or part of, the gene can be deleted. Deletions can be made in any desired region of the gene including transcribed, non-transcribed, coding and non-coding regions. Additional copies of part or all of the gene can also be introduced into a genome. Finally, alterations in nucleotide sequence can be introduced into the gene by recombinant techniques. Alterations include deletions, insertions, inversions, and point mutation. Accordingly, type II diabetes that is caused by a mutated CPE gene could be treated by introducing a functional (wild type) CPE gene into the individual. Further, specific alterations could be introduced into the gene and function tested in any given cell type, such as in cell-based models for diabetes. Still further, any given mutation can be introduced into a cell and used to form a transgenic animal which can then serve as a model for diabetes and diabetes testing.

Homologously recombinant host cells can also be produced that allow the in situ alteration of endogenous CPE polynucleotide sequences in a host cell genome. This technology is more fully described in WO 93/09222, WO 91/12650 and U.S. Pat. No. 5,641,670. Briefly, specific polynucleotide sequences corresponding to the CPE polynucleotides or sequences proximal or distal to a CPE gene are allowed to integrate into a host cell genome by homologous recombination where expression of the gene can be affected. In one embodiment, regulatory sequences are introduced that either increase or decrease expression of an endogenous sequence. Accordingly, a CPE protein can be produced in a cell not normally producing it, or increased expression of CPE protein can result in a cell normally producing the protein at a specific level.

The levels and activity of CPE RNA are also subject to modulation. Polynucleotides corresponding to any desired region of the RNA can be used directly to block transcription or translation of CPE sequences by means of antisense or ribozyme constructs. Thus, where the disorder is characterized by abnormally high gene expression, these nucleic acids can be used to decrease expression levels. A DNA antisense polynucleotide is designed to be complementary to a region of the gene involved in transcription, preventing transcription and hence production of protein. An antisense RNA or DNA polynucleotide would hybridize to the mRNA and thus block translation of mRNA into protein. An alternative technique involves cleavage by ribozymes containing nucleotide sequences complementary to one or more regions in the mRNA that attenuate the ability of the mRNA to be translated.

The invention also encompasses the modulation of nucleic acid expression using compounds that have been discovered by screening the effects of the compounds on CPE nucleic acid levels or function.

The invention is further directed to methods for modulating CPE protein levels or function. For example, where the disorder is characterized by an overexpression of the protein, antibodies or other binding partners directed against the protein can be used to block the protein function and thus functionally decrease the levels of protein present. Antibodies can be prepared against specific fragments containing sites required for function or against the intact protein. Protein levels can also be modulated by use of compounds discovered in screening techniques in which the protein levels serve as a target for effective compounds. Finally, mutant proteins can be functionally affected by the use of compounds discovered in screening techniques that use an alteration of mutant function as an end point.

Modulation can be in a cell-free system. In this context, for example, the assay could involve cleavage of substrate or other indicator of CPE activity. Modulation can also occur in cell-based systems. These cells may be permanent cell lines, cell strains, primary cultures, recombinant cells, cells derived from affected individuals, and transgenic animal models of diabetes, among others. Modulation can also be in vivo, for example, in patients having the disorder, in subjects undergoing clinical trials, and animal models of diabetes, including transgenic animal models. Modulation could be measured by direct assay of the CPE gene or gene product or by the results of CPE gene and gene product function, for example, insulin responsiveness, hepatic glucose production, insulin secretion, pro-insulin levels, and any of the functional indicators described herein and known to those of ordinary skill in the art.

All of these methods can be used to affect CPE function in individuals having or at risk for having Type II diabetes. Thus, the invention encompasses the treatment of Type II diabetes by modulating the levels or function of CPE genes or gene product.

The invention also encompasses methods for identifying compounds that interact with the CPE gene or gene product, particularly to modulate the level or function of the CPE gene or gene product. Modulation can be at the level of transcription, translation, or polypeptide function. Accordingly, where levels of CPE gene or gene product are abnormally high or low, compounds can be screened for the ability to correct the level of expression. Alternatively, where a mutation affects the function of the CPE nucleic acid or protein, compounds can be screened for their ability to compensate for or to correct the dysfunction. In this manner, CPE and CPE variants can be used to identify agonists and antagonists useful for affecting CPE and variant gene expression. These compounds can then be used to affect CPE expression or function in Type II diabetes. Thus these screening methods are useful to identify compounds that can be used for treating Type II diabetes.

These compounds are also useful in a diagnostic context in that they can then be used to identify altered levels of CPE or CPE variants in a cell, tissue, nonhuman animal, and human. For example, compounds specifically interacting with CPE nucleic acid or protein to produce a particular result, by producing that result in a cell, tissue, nonhuman animal, or human, indicate that there is a lesion in the CPE gene or gene product.

Thus, modulators of gene expression can be identified in a method wherein CPE gene or gene product is contacted with a candidate compound and the level or expression of gene or gene product is determined. The level or expression of gene or gene product in the presence of the candidate compound is compared to the level or expression of gene or gene product in the absence of the candidate compound. The candidate compound can then be identified as a modulator of nucleic acid or protein expression based on this comparison and be used, for example, to treat type II diabetes. When the level or expression of gene or gene product is statistically significantly greater in the presence of the candidate compound than in its absence, the candidate compound is identified as a stimulator of levels or expression of the gene or gene product. When levels or product expression are statistically significantly less in the presence of the candidate compound than in its absence, the candidate compound is identified as an inhibitor.

These compounds can be used to test on model systems, including animal models of diabetes, and human clinical trial subjects, cells derived from these sources as well as transgenic animal models of diabetes.

Accordingly, the invention provides methods of treatment, with the gene or gene product as a target, using a compound identified through drug screening as a modulator to modulate expression of the gene or gene product. Modulation includes both up-regulation (i.e. activation or agonization) or down-regulation (suppression or antagonization) or nucleic acid expression.

Further, the expression of genes that are up- or down-regulated in response to CPE can also be assayed. In this embodiment the regulatory regions of these genes can be operably linked to a reporter gene such as luciferase.

Candidate compounds include, for example, 1) peptides such as soluble peptides, including Ig-tailed fusion peptides and members of random peptide libraries (see, e.g., Lam et al., Nature 354:82–84 (1991); Houghten et al., Nature 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., Cell 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

Other candidate compounds include preprocessed peptides that are normal substrates for CPE, for example, enkephalin, insulin, and proneurotensin, i.e., peptides treated so that the amino terminal basic residues have been cleaved.

Any of the biological or biochemical functions mediated by CPE can be used in an endpoint assay. These include all of the biochemical or biochemical/biological events described herein, in the references cited herein, incorporated by reference for these endpoint assay targets, and other functions known to those of ordinary skill in the art.

A further aspect of the invention involves pharmacogenomic analysis in the case of polymorphic CPE proteins and specific mutants. Pharmacogenomics deal with clinically significant hereditary variations in the response to drugs due to altered drug disposition and abnormal action in affected persons. See, e.g., Eichelbaum, M., Clin. Exp. Pharmacol. Physiol. 23(10–11):983–985 (1996), and Linder, M. W., Clin. Chem. 43(2):254–266 (1997). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. Accordingly, in one aspect of the invention, natural variants of the CPE protein are used to screen for compounds that are effective against a given allele and are not toxic to the specific patient. Compounds can thus be classed according to their effects against naturally occurring allelic variants. This allows more effective treatment and diagnosis of type II diabetes.

Test systems for identifying compounds include both cell-free and cell-based systems derived from normal and affected tissue, cell lines and strains, primary cultures, animal diabetes models, and including transgenic animals. Naturally-occurring cells will express abnormal levels of CPE gene or gene product or variants of CPE genes or gene products. Alternatively, these cells can provide recombinant hosts for the expression of desired levels of CPE gene or gene product or variants of CPE gene or gene product. A cell-free system can be used, for example, when assessing the effective agents on nucleic acid or polypeptide function.

For example, in a cell-free system, competition binding assays are designed to discover compounds that interact with the polypeptide. Thus, a compound is exposed to the polypeptide under conditions that allow the compound to bind or to otherwise interact with the polypeptide. Soluble polypeptide is also added to the mixture. If the test compound interacts with the soluble polypeptide, it decreases the amount of complex formed or activity from the target. This type of assay is particularly useful in cases in which compounds are sought that interact with specific regions of the polypeptide. Thus, the soluble polypeptide that competes with the target region is designed to contain peptide sequences corresponding to the region of interest. In one embodiment, the region of interest is the 51 C-terminal amino acids that direct sorting to the membrane. Another region is that located around 23–33 amino acids from the C-terminal region, required for proper folding. A third region is located within the predicted amphiphilic helix of the C-terminal 14 amino acid residues, involved in binding CPE to membranes.

To perform cell-free drug screening assays, it is desirable to immobilize either the protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase/CPE fusion proteins can be adsorbed onto glutathione sepharose beads Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of CPE-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a CPE-binding protein and a candidate compound are incubated in the CPE protein-presenting wells and the amount of complex trapped in the well can be quantitated. Methods for detecting such complexes, in addition to those described above for the GST-immobilized complexes, include immunodetection of complexes using antibodies reactive with the CPE protein target molecule, or which are reactive with the CPE protein and compete with the target molecule; as well as enzyme-linked assays which rely on detecting an enzymatic activity associated with the target molecule.

Cell-based systems include assay of individual cells or assay of cells in a tissue sample or in vivo. Drug screening assays can be cell-based or cell-free systems. Cell-based systems can be native, i.e., cells that normally express the protein, as a biopsy or expanded in cell culture. In one embodiment, however, cell-based assays involve recombinant host cells expressing the protein. In vivo test systems include, not only individuals involved in clinical trials, but also animal diabetes models, including transgenic animals. Single cells include recombinant host cells in which desired altered CPE gene or gene products have been introduced. These host cells can express abnormally high or low levels of the CPE gene or gene product or mutant versions of the CPE gene or gene product. Thus, the recombinant cells can be used as test systems for identifying compounds that have the desired effect on the altered gene or gene product. Mutations can be naturally occurring or constructed for their effect on the course or development of type II diabetes, for example, determined by the model test systems discussed further below. Similarly, naturally-occurring or designed mutations can be introduced into transgenic animals, which then serve as an in vivo test system to identify compounds having a desired effect on CPE gene or gene product.

In yet another aspect of the invention, the polypeptides can be used in a "two hybrid" assay (see, for example, U.S. Pat. No. 5,283,317; Zervos et al. (1993) *Cell* 72:223–232; Madura et al. (1993) *Oncogene* 8:1693–1696; and Brent WO94/10300), for isolating coding sequences for other cellular proteins which bind to or interact with CPE.

Briefly, the two hybrid assay relies on reconstituting in vivo a functional transcriptional activator protein from two separate fusion proteins. In particular, the method makes use of chimeric genes which express hybrid proteins. To illustrate, a first hybrid gene comprises the coding sequence for a DNA-binding domain of a transcriptional activator fused in frame to the coding sequence for a CPE polypeptide. The second hybrid protein encodes a transcriptional activation domain fused in frame to a sample gene from a cDNA library. If the bait and sample hybrid proteins are able to interact, e.g., form a CPE-dependent complex, they bring into close proximity the two domains of the transcriptional activator. This proximity is sufficient to cause transcription of a reporter gene which is operably linked to a transcriptional regulatory site responsive to the transcriptional activator, and expression of the reporter gene can be detected and used to score for the interaction of CPE and sample proteins.

Modulators of CPE gene or gene product identified according to these assays can be used to treat type II diabetes by treating cells that aberrantly express the gene or gene product. These methods of treatment include the steps of administering the modulators of protein activity in a pharmaceutical composition as described herein, to a subject in need of such treatment.

The invention thus provides a method for identifying a compound that can be used to treat type II diabetes. The method typically includes assaying the ability of the compound to modulate the expression of the CPE gene or gene product to identify a compound that can be used to treat the disorder.

The invention is also directed to CPE genes or gene products containing alterations that correlate with Type II diabetes. These altered genes or gene products can be isolated and purified or can be created in situ, for example, by means of in situ gene replacement techniques. In the gene, alterations of this type can be found in any site, transcribed, nontranscribed, coding, and noncoding. Likewise, in the RNA, alterations can be found in both the coding and noncoding regions. In a specific disclosed embodiment, the invention encompasses a coding mutation, arg→trp 283, corresponding to a c→t nucleotide change at this position. In one embodiment, the carboxypeptidase E gene or gene product comprises a fragment, preferably a fragment containing the mutation. The invention thus encompasses primers, both wild type and variant, that are useful in the methods described herein. Similarly, ribozymes and antisense nucleic acids can be derived from variants that correlate with type II diabetes or can be derived from the wild type and used in the methods described herein.

The genes and gene products are useful in pharmaceutical compositions for diagnosing or modulating the level or expression of CPE gene or gene product in vivo, as in individual patients treated for type II diabetes, subjects in clinical trials, animal diabetes models, and transgenic animal diabetes models. Thus, these pharmaceutical compositions are useful for testing and treatment. The CPE genes or gene products are also useful for otherwise modulating expression of the gene or gene product in cell-free or cell-based systems in vitro. They are further useful in ex vivo applications. The genes and gene products are also useful for creating model test systems for type II diabetes, for example, recombinant cells, tissues, and animals. The genes and gene products are also useful in a diagnostic context as comparisons for other naturally-occurring variation in the CPE gene or gene product. Accordingly, these reagents can form the basis for a diagnostic kit. Further, specific variants (mutants) are useful for testing compounds that may be effective in the treatment or diagnosis of type II diabetes. Such mutants can also form the basis of a reagent in a test kit, particularly for introduction into a desired cell type or transgenic animal for drug testing. Accordingly, the invention is also directed to isolated and purified polypeptides and polynucleotides.

The invention is thus directed to compositions based on carboxypeptidase E genes or gene products. Compositions also include nucleic acid primers derived from carboxypeptidase E mutants, antisense nucleotides derived from these mutants, and ribozymes based on the mutations, and antibodies specific for the mutants. Compositions further include recombinant cells containing any of the mutants, vectors containing the mutants, cells expressing the mutants, fragments of the mutants, and antibodies or other binding partners that specifically recognize the mutation. These compositions can all be combined with a pharmaceutically acceptable carrier to create pharmaceutical compositions useful for detecting or modulating the level or expression of carboxypeptidase E gene or gene product and thereby diagnosing or treating Type II diabetes.

As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide, however, can be joined to another polypeptide with which it is not normally associated in a cell and still be considered "isolated" or "purified."The CPE polypeptides can be purified to homogeneity. It is understood, however, that preparations in which the polypeptide is not purified to homogeneity are useful and considered to contain an isolated form of the polypeptide. The critical feature is that the preparation allows for the desired function of the polypeptide, even in the presence of considerable amounts of other components. Thus, the invention encompasses various degrees of purity.

In one embodiment, the language "substantially free of cellular material" includes preparations of the polypeptide having less than about 30% (by dry weight) other proteins (i.e., contaminating protein), less than about 20% other proteins, less than about 10% other proteins, or less than about 5% other proteins. When the CPE polypeptide is recombinantly produced, it can also be substantially free of culture medium, i.e., culture medium represents less than about 20%, less than about 10%, or less than about 5% of the volume of the protein preparation.

The language "substantially free of chemical precursors or other chemicals" includes preparations of the polypeptide in which it is separated from chemical precursors or other chemicals that are involved in its synthesis. In one embodiment, the language "substantially free of chemical precursors or other chemicals" includes preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

Variants can be naturally-occurring or can be made by recombinant means or chemical synthesis to provide useful and novel characteristics for the polypeptide. This includes preventing immunogenicity from pharmaceutical formulations by preventing protein aggregation.

Useful variations further include alteration of binding characteristics. For example, one embodiment involves a variation at the binding site that results in binding but not release, or slower release, of substrate. A further useful variation at the same sites can result in a higher affinity for substrate. Useful variations also include changes that provide for affinity for another substrate. Another useful variation includes one that allows binding but which reduces cleavage of the substrate.

Amino acids that are essential for function can be identified by methods known in the art, such as site-directed mutagenesis or alanine-scanning mutagenesis (Cunningham et al., *Science* 244:1081–1085 (1989)). The latter procedure introduces single alanine mutations at every residue in the molecule. The resulting mutant molecules are then tested for biological activity. Sites that are critical can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The invention also provides antibodies that selectively bind to the protein. An antibody is considered to selectively bind, even if it also binds to other proteins that are not substantially homologous with the protein. These other proteins share homology with a fragment or domain of the protein. This conservation in specific regions gives rise to antibodies that bind to both proteins by virtue of the homologous sequence. In this case, it would be understood that antibody binding to the CPE protein is still selective.

To generate antibodies, an isolated polypeptide is used as an immunogen to generate antibodies using standard techniques for polyclonal and monoclonal antibody preparation. Either the full-length protein or antigenic peptide fragment can be used.

Antibodies are preferably prepared from these regions or from discrete fragments in these regions. However, antibodies can be prepared from any region of the peptide as described herein. A preferred fragment produces an antibody that diminishes or completely prevents substrate-binding. Antibodies can be developed against the entire protein or portions of the protein, for example, the substrate binding domain.

Antibodies can be polyclonal or monoclonal. An intact antibody, or a fragment thereof (e.g. Fab or $F(ab')_2$) can be used.

Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

An appropriate immunogenic preparation can be derived from native, recombinantly expressed, protein or chemically synthesized peptides.

The antibodies can be used to isolate a CPE protein by standard techniques, such as affinity chromatography or immunoprecipitation. The antibodies can facilitate the purification of the natural protein from cells and recombinantly-produced protein expressed in host cells.

The antibodies are useful to detect the presence of protein in cells or tissues to determine the pattern of expression of the protein among various tissues in an organism.

The antibodies can be used to detect the protein in situ, in vitro, or in a cell lysate or supernatant in order to evaluate the abundance and pattern of expression.

The antibodies can be used to assess abnormal tissue distribution or abnormal expression during development.

Antibody detection of circulating fragments of the full length CPE protein can be used to identify CPE turnover.

Further, the antibodies can be used to assess CPE expression in active stages of diabetes or in an individual with a predisposition toward diabetes. When the disorder is caused by an inappropriate tissue distribution, developmental expression, or level of expression of the CPE protein, the antibody can be prepared against the normal CPE protein. If a disorder is characterized by a specific mutation in the CPE protein, antibodies specific for this mutant protein can be used to assay for the presence of the specific mutant CPE protein. However, intracellularly-made antibodies ("intrabodies") are also encompassed, which would recognize intracellular CPE peptide regions.

The antibodies can also be used to assess normal and aberrant subcellular localization of cells in the various tissues in an organism. Antibodies can be developed against the whole CPE or portions of the CPE.

The diagnostic uses can be applied, not only in genetic testing, but also in monitoring a treatment modality. Accordingly, where treatment is ultimately aimed at correcting CPE expression level or the presence of aberrant CPE and aberrant tissue distribution or developmental expression, antibodies directed against the CPE or relevant fragments can be used to monitor therapeutic efficacy.

The antibodies are also useful for inhibiting CPE function. These uses can also be applied in a therapeutic context. Antibodies can be prepared against specific fragments containing sites required for function or against intact CPE associated with a cell.

An "isolated" CPE nucleic acid is one that is separated from other nucleic acid present in the natural source of the CPE nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5KB. The important point is that the nucleic acid is isolated from flanking sequences such that it can be subjected to the specific manipulations described herein such as recombinant expression, preparation of probes and primers, and other uses specific to the nucleic acid sequences.

Moreover, an "isolated" nucleic acid molecule, such as a cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

The CPE polynucleotides can encode the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

The CPE polynucleotides include, but are not limited to, the sequence encoding the mature polypeptide alone, the sequence encoding the mature polypeptide and additional coding sequences, such as a leader or secretory sequence (e.g., a pre-pro or pro-protein sequence), the sequence encoding the mature polypeptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the polynucleotide may be fused to a marker sequence encoding, for example, a peptide that facilitates purification.

Polynucleotides can be in the form of RNA, such as mRNA, or in the form DNA, including cDNA and genomic DNA obtained by cloning or produced by chemical synthetic techniques or by a combination thereof The nucleic acid, especially DNA, can be double-stranded or single-stranded. Single-stranded nucleic acid can be the coding strand (sense strand) or the non-coding strand (anti-sense strand).

The invention also provides CPE nucleic acid molecules encoding the variant polypeptides described herein. Such polynucleotides may be naturally-occurring, such as allelic variants (same locus), homologs (different locus), and orthologs (different organism), or may be constructed by recombinant DNA methods or by chemical synthesis. Such non-naturally occurring variants may be made by mutagenesis techniques, including those applied to polynucleotides, cells, or organisms. Accordingly, as discussed above, the variants can contain nucleotide substitutions, deletions, inversions and insertions.

Variation can occur in either or both the coding and non-coding regions. The variations can produce both conservative and non-conservative amino acid substitutions.

Furthermore, the invention provides polynucleotides that comprise a fragment of the full length CPE polynucleotides. The fragment can be single or double stranded and can comprise DNA or RNA. The fragment can be derived from either the coding or the non-coding sequence.

The invention also provides CPE nucleic acid fragments that encode epitope bearing regions of the CPE proteins described herein.

The invention also provides vectors containing the CPE polynucleotides. The term "vector" refers to a vehicle, preferably a nucleic acid molecule, that can transport the CPE polynucleotides. When the vector is a nucleic acid molecule, the CPE polynucleotides are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the CPE polynucleotides. Alternatively, the vector may integrate into the host cell genome and produce additional copies of the CPE polynucleotides when the host cell replicates.

The invention provides vectors for the maintenance (cloning vectors) or vectors for expression (expression vectors) of the CPE polynucleotides. The vectors can function in prokaryotic or eukaryotic cells or in both (shuttle vectors).

Expression vectors contain cis-acting regulatory regions that are operably linked in the vector to the CPE polynucleotides such that transcription of the polynucleotides is allowed in a host cell. The polynucleotides can be introduced into the host cell with a separate polynucleotide capable of affecting transcription. Thus, the second polynucleotide may provide a trans-acting factor interacting with the cis-regulatory control region to allow transcription of the CPE polynucleotides from the vector. Alternatively, a trans-acting factor may be supplied by the host cell. Finally, a transacting factor can be produced from the vector itself.

It is understood, however, that in some embodiments, transcription and/or translation of the CPE polynucleotides can occur in a cell free system.

The regulatory sequence to which the polynucleotides described herein can be operably linked include promoters for directing mRNA transcription. These include, but are not limited to, the left promoter from bacteriophage λ, the lac, TRP, and TAC promoters from *E. coli,* the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd. ed., Cold Spring Harbor Laboratory Press, Cold Spring Harbor, N.Y., (1989).

A variety of expression vectors can be used to express a CPE polynucleotide. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual.* 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The CPE polynucleotides can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate polynucleotide can be introduced into an appropriate host cell for propagation or expression using well-known techniques. Bacterial cells include, but are not limited to, *E. coli,* Streptomyces, and *Salmonella typhimurium.* Eukaryotic cells include, but are not limited to, yeast, insect cells such as Drosophila, animal cells such as COS and CHO cells, and plant cells.

As described herein, it may be desirable to express the polypeptide as a fusion protein. Accordingly, the invention provides fusion vectors that allow for the production of the CPE polypeptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired polypeptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in a host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the polynucleotide of interest can be altered to provide preferential codon usage for a specific host cell, for example *E. coli.* (Wada et al., *Nucleic Acids Res.* 20:2111–2118 (1992)).

The CPE polynucleotides can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The CPE polynucleotides can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the polynucleotides described herein are expressed in mammalian cells using mammalian expression vectors. Examples of mammalian expression vectors include pCDM8 (Seed, B. *Nature* 329:840(1987)) and pMT2PC (Kaufman et al, *EMBO J.* 6:187–195 (1987)).

The expression vectors listed herein are provided by way of example only of the well-known vectors available to those of ordinary skill in the art that would be useful to express the CPE polynucleotides. The person of ordinary skill in the art would be aware of other vectors suitable for maintenance propagation or expression of the polynucleotides described herein. These are found for example in Sambrook, J., Fritsh, E. F., and Maniatis, T. *Molecular Cloning: A Laboratory Manual* 2nd, ed., Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the polynucleotide sequences described herein, including both coding and noncoding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the CPE polynucleotides can be introduced either alone or with other polynucleotides that are not related to the CPE polynucleotides such as those providing trans-acting factors for expression vectors. When more than one vector is introduced into a cell, the vectors can be introduced independently, co-introduced or joined to the CPE polynucleotide vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the polynucleotides described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell free transcription and translation systems can also be used to produce these proteins using RNA derived from the DNA constructs described herein.

Where secretion of the polypeptide is desired, appropriate secretion signals are incorporated into the vector. The signal sequence can be endogenous to the CPE polypeptides or heterologous to these polypeptides.

Where the polypeptide is not secreted into the medium, the protein can be isolated from the host cell by standard disruption procedures, including freeze thaw, sonication, mechanical disruption, use of lysing agents and the like. The polypeptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the polypeptides described herein, the polypeptides can have various glycosylation patterns, depending upon the cell, or maybe non-glycosylated as when produced in bacteria. In addition, the polypeptides may include an initial modified methionine in some cases as a result of a host-mediated process.

The host cells expressing the polypeptides described herein, and particularly recombinant host cells, have a variety of uses. First, the cells are useful for producing CPE proteins or polypeptides that can be further purified to produce desired amounts of CPE protein or fragments. Thus, host cells containing expression vectors are useful for polypeptide production.

Host cells are also useful for conducting cell based assays involving the CPE or CPE fragments. Thus, a recombinant host cell expressing a native CPE is useful to assay for compounds that stimulate or inhibit CPE function.

Host cells are also useful for identifying CPE mutants in which these functions are affected. If the mutants naturally occur, host cells containing the mutations are useful to assay compounds that have a desired effect on the mutant CPE (for example, stimulating or inhibiting function) which may not be indicated by their effect on the native CPE.

Recombinant host cells are also useful for expressing the chimeric polypeptides described herein to assess compounds that activate or suppress activation by means of a heterologous amino terminal extracellular domain (or other binding region). Alternatively, a heterologous region spanning the entire transmembrane domain (or parts thereof) can be used to assess the effect of a desired amino terminal extracellular domain (or other binding region) on any given host cell. In this embodiment, a region spanning the entire transmembrane domain (or parts thereof) compatible with the specific host cell is used to make the chimeric vector. Alternatively, a heterologous carboxy terminal intracellular, e.g., signal transduction, domain can be introduced into the host cell.

Further, mutant CPEs can be designed in which one or more of the various functions is engineered to be increased or decreased used to augment or replace CPE proteins in an individual. Thus, host cells can provide a therapeutic benefit by replacing an aberrant CPE or providing an aberrant CPE that provides a therapeutic result. In one embodiment, the cells provide CPE that is abnormally active.

Homologously recombinant host cells can also be produced that allow the in situ alteration of endogenous CPE polynucleotide sequences in a host cell genome. This technology is more fully described in WO 93/09222, WO 91/12650 and U.S. Pat. No. 5,641,670. Briefly, specific polynucleotide sequences corresponding to the CPE polynucleotides or sequences proximal or distal to a CPE gene are allowed to integrate into a host cell genome by homologous recombination where expression of the gene can be affected. In one embodiment, regulatory sequences are introduced that either increase or decrease expression of an endogenous sequence. Accordingly, a CPE protein can be produced in a cell not normally producing it, or increased expression of CPE protein can result in a cell normally producing the protein at a specific level.

In one embodiment, the host cell can be a fertilized oocyte or embryonic stem cell that can be used to produce a transgenic animal containing the altered CPE gene. Alternatively, the host cell can be a stem cell or other early tissue precursor that gives rise to a specific subset of cells and can be used to produce transgenic tissues in an animal. See also Thomas et al., *Cell* 51:503 (1987) for a description of homologous recombination vectors. The vector is introduced into an embryonic stem cell line (e.g., by electroporation) and cells in which the introduced gene has homologously recombined with the endogenous CPE gene is selected (see e.g., Li, E. et al., *Cell* 69:915 (1992)). The selected cells are then injected into a blastocyst of an animal (e.g., a mouse) to form aggregation chimeras (see e.g., Bradley, A. in *Teratocarcinomas and Embryonic Stem Cells: A Practical Approach,* E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos. WO 90/11354; WO 91/01140; and WO 93/04169.

The genetically engineered host cells can be used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a CPE protein and identifying and evaluating modulators of CPE protein activity.

Other examples of transgenic animals include non-human primates, sheep, dogs, cows, goats, chickens, and amphibians.

In one embodiment, a host cell is a fertilized oocyte or an embryonic stem cell into which CPE polynucleotide sequences have been introduced.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the CPE nucleotide sequences described herein, especially the altered sequences, can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the CPE protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals caring a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter GO phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to a pseudopregnant female foster animal. The offspring born of this female foster animal will be a clone of the animal from which the cell, e.g., the somatic cell, is isolated.

Transgenic animals containing recombinant cells that express the polypeptides described herein are useful to conduct the assays described herein in an in vivo context. Accordingly, the various physiological factors that are present in vivo and that could effect ligand binding, CPE activation, and signal transduction, may not be evident from in vitro cell free or cell based assays. Accordingly, it is useful to provide non-human transgenic animals to assay in vivo CPE function, the effect of specific mutant CPEs on CPE function, and the effect of chimeric CPEs. It is also possible to assess the effect of null mutations, that is mutations that substantially or completely eliminate one or more CPE functions.

The CPE nucleic acid molecules, protein (particularly fragments, such as the domains that interact with other cellular components), modulators of the nucleic acid and protein, and especially binding partners, and antibodies (also referred to herein as "active compounds") can be incorporated into pharmaceutical compositions suitable for administration to a subject, e.g., a human. Such compositions typically comprise the nucleic acid molecule, protein, modulator, or antibody and a pharmaceutically acceptable carrier.

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions. A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a CPE protein or anti-CPE antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see e.g., Chen et al., *PNAS* 91:3054–3057 (1994)). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

This invention may be embodied in many different forms and should not be construed as limited to the embodiments set forth herein; rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

That which is claimed:

1. A method for detecting a mutation in the carboxypeptidase E (CPE) gene in a mammal having or predisposed to having type II diabetes, said method comprising:
    (a) obtaining a biological sample from a mammal having, or predisposed to having, type II diabetes, said sample containing a CPE gene; and
    (b) detecting an alteration in said CPE gene, wherein said alteration is a mutation in the coding region of said gene and said mutation results in an arginine to a tryptophan substitution at amino acid 283, which corresponds to a C to T nucleotide substitution.

2. A method of diagnosing type II diabetes or predisposition to having type II diabetes in a mammal, said method comprising:
    (a) obtaining a biological sample from said mammal, said sample containing carboxypeptidase E (CPE) gene; and
    (b) identifying an alteration in carboxypeptidase E gene, wherein said alteration is a mutation in the coding region of said gene and said mutation results in an arginine to a tryptophan substitution at amino acid 283, which corresponds to a C to T nucleotide substitution.

3. A method for determining whether a human subject has or is at risk for developing type H diabetes comprising the steps of:
    (a) obtaining a sample from the human subject, said sample comprising nucleic acid molecules containing a carboxypeptidase E (CPE) gene; and
    (b) detecting the presence or absence of a genetic mutation in the gene of said subject, wherein said genetic mutation comprises an alteration in the codon which codes for amino acid 283 which results in a replacement of arginine by tryptophan and the presence of said genetic mutation identifies a subject that has or is at risk for developing type II diabetes.

4. A method for determining whether a human subject bas or is at risk for developing type II diabetes comprising the steps of:
    (a) obtaining a sample from the human subject, said sample comprising nucleic acid molecules containing a carboxypeptidase B (CPE) gene; and
    (b) detecting the presence or absence of a genetic mutation in the gene of said subject, wherein said genetic mutation comprises an alteration in the codon beginning at nucleotide 1133 of the nucleotide sequence shown in FIG. 1 (SEQ ID NO: 1), which results in a replacement of arginine by tryptophan.

5. A method for detecting a mutation in the carboxypeptidase E (CPE) gene product in a mammal having or predisposed to having type II diabetes, said method comprising:
    (a) obtaining a biological sample from a mammal having, or predisposed to having, type II diabetes, said sample containing a CPE gene product; and
    (b) detecting an alteration in said CPE gene product, wherein said alteration is an arginine to a tryptophan substitution at amino acid 283.

6. A method of diagnosing type II diabetes in a mammal, said method comprising:
    (a) obtaining a biological sample from said mammal, said sample containing carboxypeptidase E (CPE) gene product; and
    (b) identifying an alteration in carboxypeptidase E gene product, wherein said alteration is an arginine to a tryptophan substitution at amino acid 283.

* * * * *

UNITED STATES PATENT AND TRADEMARK OFFICE
CERTIFICATE OF CORRECTION

PATENT NO. : 6,248,527 B1  
DATED : June 19, 2001  
INVENTOR(S) : Chen et al.

Page 1 of 1

It is certified that error appears in the above-identified patent and that said Letters Patent is hereby corrected as shown below:

<u>Column 57,</u>  
Line 37, "type H" should read -- type II --.

<u>Column 58,</u>  
Line 14, "bas" should read -- has --;  
Line 19, "B" should read -- E --.

Signed and Sealed this

Sixteenth Day of April, 2002

Attest:

*Attesting Officer*

JAMES E. ROGAN  
*Director of the United States Patent and Trademark Office*

SEQUENCE LISTING

```
<160> NUMBER OF SEQ ID NOS: 10

<210> SEQ ID NO: 1
<211> LENGTH: 2439
<212> TYPE: DNA
<213> ORGANISM: Homo sapiens
<220> FEATURE:
<221> NAME/KEY: CDS
<222> LOCATION: (287)..(1714)
<220> FEATURE:
<223> OTHER INFORMATION: carboxypeptidase E

<400> SEQUENCE: 1
ggcgtgcccg tctctccgcc ggcccctgc ctcgcagtgg tttctcctgc agctcccctg      60
ggctccgcgg ccagtagtgc agcccgtgga gccgcggctt tgcccgtctc ctctgggtgg     120
ccccagtgcg cgggctgaca ctcattcagc cggggaaggt gaggcgagta gaggctggtg     180
cggaacttgc cgcccccagc agcgccggcg ggctaagccc agggccgggc agacaaaaga     240
ggccgcccgc gtaggaaggc acggccggcg gcggcggagc gcagcg atg gcc ggg        295
                                                    Met Ala Gly
                                                     1 cga ggg ggc agc gcg ctg ctg gct ctg tgc ggg gca ctg gct gcc tgc      343
Arg Gly Gly Ser Ala Leu Leu Ala Leu Cys Gly Ala Leu Ala Ala Cys
      5                  10                  15 ggg tgg ctc ctg ggc gcc gaa gcc cag gag ccc ggg gcg ccc gcg gcg      391
Gly Trp Leu Leu Gly Ala Glu Ala Gln Glu Pro Gly Ala Pro Ala Ala
 20                  25                  30                  35 ggc atg agg cgg cgc cgg cgg ctg cag caa gag gac ggc atc tcc ttc      439
Gly Met Arg Arg Arg Arg Arg Leu Gln Gln Glu Asp Gly Ile Ser Phe
                  40                  45                  50 gag tac cac cgc tac ccc gag ctg cgc gag gcg ctc gtg tcc gtg tgg      487
Glu Tyr His Arg Tyr Pro Glu Leu Arg Glu Ala Leu Val Ser Val Trp
              55                  60                  65 ctg cag tgc acc gcc atc agc agg att tac acg gtg ggg cgc agc ttc      535
Leu Gln Cys Thr Ala Ile Ser Arg Ile Tyr Thr Val Gly Arg Ser Phe
          70                  75                  80 gag ggc cgg gag ctc ctg gtc atc gag ctg tcc gac aac cct ggc gtc      583
Glu Gly Arg Glu Leu Leu Val Ile Glu Leu Ser Asp Asn Pro Gly Val
      85                  90                  95 cat gag cct ggt gag cct gaa ttt aaa tac att ggg aat atg cat ggg      631
His Glu Pro Gly Glu Pro Glu Phe Lys Tyr Ile Gly Asn Met His Gly
100                 105                 110                 115 aat gag gct gtt gga cga gaa ctc ctc att ttc ttg gcc cag tac cta      679
Asn Glu Ala Val Gly Arg Glu Leu Leu Ile Phe Leu Ala Gln Tyr Leu
                 120                 125                 130 tgc aac gaa tac cag aag ggg aac gag aca att gtc aac ctg atc cac      727
Cys Asn Glu Tyr Gln Lys Gly Asn Glu Thr Ile Val Asn Leu Ile His
             135                 140                 145
```

-continued

| | | |
|---|---|---|
| agt acc cgc att cac atc atg cct tcc ctg aac cca gat ggc ttt gag<br>Ser Thr Arg Ile His Ile Met Pro Ser Leu Asn Pro Asp Gly Phe Glu<br>150                        155                    160 | 775 |
| aag gca gcg tct cag cct ggt gaa ctc aag gac tgg ttt gtg ggt cga<br>Lys Ala Ala Ser Gln Pro Gly Glu Leu Lys Asp Trp Phe Val Gly Arg<br>    165                    170                    175 | 823 |
| agc aat gcc cag gga ata gat ctg aac cgg aac ttt cca gac ctg gat<br>Ser Asn Ala Gln Gly Ile Asp Leu Asn Arg Asn Phe Pro Asp Leu Asp<br>180                        185                    190                    195 | 871 |
| agg ata gtg tac gtg aat gag aaa gaa ggt ggt cca aat aat cat ctg<br>Arg Ile Val Tyr Val Asn Glu Lys Glu Gly Gly Pro Asn Asn His Leu<br>                    200                    205                    210 | 919 |
| ttg aaa aat atg aag aaa att gtg gat caa aac aca aag ctt gct cct<br>Leu Lys Asn Met Lys Lys Ile Val Asp Gln Asn Thr Lys Leu Ala Pro<br>215                        220                    225 | 967 |
| gag acc aag gct gtc att cat tgg att atg gat att cct ttt gtg ctt<br>Glu Thr Lys Ala Val Ile His Trp Ile Met Asp Ile Pro Phe Val Leu<br>            230                    235                    240 | 1015 |
| tct gcc aat ctc cat gga gga gac ctt gtg gcc aat tat cca tat gat<br>Ser Ala Asn Leu His Gly Gly Asp Leu Val Ala Asn Tyr Pro Tyr Asp<br>245                        250                    255 | 1063 |
| gag acg cgg agt ggt agt gct cac gaa tac agc tcc tcc cca gat gac<br>Glu Thr Arg Ser Gly Ser Ala His Glu Tyr Ser Ser Ser Pro Asp Asp<br>260                        265                    270                    275 | 1111 |
| gcc att ttc caa agc ttg gcc cgg gca tac tct tct ttc aac ccg gcc<br>Ala Ile Phe Gln Ser Leu Ala Arg Ala Tyr Ser Ser Phe Asn Pro Ala<br>                    280                    285                    290 | 1159 |
| atg tct gac ccc aat cgg cca cca tgt cgc aag aat gat gat gac agc<br>Met Ser Asp Pro Asn Arg Pro Pro Cys Arg Lys Asn Asp Asp Asp Ser<br>                    295                    300                    305 | 1207 |
| agc ttt gta gat gga acc acc aac ggt ggt gct tgg tac agc gta cct<br>Ser Phe Val Asp Gly Thr Thr Asn Gly Gly Ala Trp Tyr Ser Val Pro<br>310                        315                    320 | 1255 |
| gga ggg atg caa gac ttc aat tac ctt agc agc aac tgt ttt gag atc<br>Gly Gly Met Gln Asp Phe Asn Tyr Leu Ser Ser Asn Cys Phe Glu Ile<br>325                        330                    335 | 1303 |
| acc gtg gag ctt agc tgt gag aag ttc cca cct gaa gag act ctg aag<br>Thr Val Glu Leu Ser Cys Glu Lys Phe Pro Pro Glu Glu Thr Leu Lys<br>340                        345                    350                    355 | 1351 |
| acc tac tgg gag gat aac aaa aac tcc ctc att agc tac ctt gag cag<br>Thr Tyr Trp Glu Asp Asn Lys Asn Ser Leu Ile Ser Tyr Leu Glu Gln<br>                    360                    365                    370 | 1399 |
| ata cac cga gga gtt aaa gga ttt gtc cga gac ctt caa ggt aac cca<br>Ile His Arg Gly Val Lys Gly Phe Val Arg Asp Leu Gln Gly Asn Pro<br>375                        380                    385 | 1447 |
| att gcg aat gcc acc atc tcc gtg gaa gga ata gac cac gat gtt aca<br>Ile Ala Asn Ala Thr Ile Ser Val Glu Gly Ile Asp His Asp Val Thr<br>390                        395                    400 | 1495 |
| tcc gca aag gat ggt gat tac tgg aga ttg ctt ata cct gga aac tat<br>Ser Ala Lys Asp Gly Asp Tyr Trp Arg Leu Leu Ile Pro Gly Asn Tyr<br>405                        410                    415 | 1543 |
| aaa ctt aca gcc tca gct cca ggc tat ctg gca ata aca aag aaa gtg<br>Lys Leu Thr Ala Ser Ala Pro Gly Tyr Leu Ala Ile Thr Lys Lys Val<br>420                        425                    430                    435 | 1591 |
| gca gtt cct tac agc cct gct gct ggg gtt gat ttt gaa ctg gag tca<br>Ala Val Pro Tyr Ser Pro Ala Ala Gly Val Asp Phe Glu Leu Glu Ser<br>                    440                    445                    450 | 1639 |
| ttt tct gaa agg aaa gaa gag aag gaa gaa ttg atg gaa tgg tgg<br>Phe Ser Glu Arg Lys Glu Glu Lys Glu Glu Leu Met Glu Trp Trp<br>                    455                    460                    465 | 1687 |

```
aaa atg atg tca gaa act tta aat ttt taaaaaggct tctagttagc    1734
Lys Met Met Ser Glu Thr Leu Asn Phe
            470                 475 tgctttaaat ctatctatat aatgtagtat gatgtaatgt ggtctttttt ttagattttg    1794
tgcagttaat acttaacatt gatttatttt ttaatcattt aaatattaat caactttcct    1854
taaaataaat agcctcttag gtaaaaatat aagaacttga tatatttcat tctcttatat    1914
agtattcatt ttcctaccta tattacacaa aaaagtatag aaaagattta agtaattttg    1974
ccatcctagg cttaaatgca atattcctgg tattatttac aatgcagaat tttttgagta    2034
attctagctt tcaaaaatta gtgaagttct tttactgtaa ttggtgacaa tgtcacataa    2094
tgaatgctat tgaaaaggtt aacagataca gctcggagtt gtgagcactc tactgcaaga    2154
cttaaatagt tcagtataaa ttgtcgtttt tttcttgtgc tgactaacta taagcatgat    2214
cttgttaatg cattttttgat gggaagaaaa ggtacatgtt tacaaagagg ttttatgaaa    2274
agaataaaaa ttgacttctt gcttgtacat ataggagcaa tactattata ttatgtagtc    2334
cgttaacact acttaaaagt ttagggtttt ctcttggttg tagagtggcc cagaattgca    2394
ttctgaatga ataaaggtta aaaaaaaatc cccagtgaaa aaaaa                    2439

<210> SEQ ID NO: 2
<211> LENGTH: 476
<212> TYPE: PRT
<213> ORGANISM: Homo sapiens

<400> SEQUENCE: 2

Met Ala Gly Arg Gly Gly Ser Ala Leu Leu Ala Leu Cys Gly Ala Leu
  1               5                  10                  15

Ala Ala Cys Gly Trp Leu Leu Gly Ala Glu Ala Gln Glu Pro Gly Ala
                 20                  25                  30

Pro Ala Ala Gly Met Arg Arg Arg Arg Leu Gln Gln Glu Asp Gly
             35                  40                  45

Ile Ser Phe Glu Tyr His Arg Tyr Pro Glu Leu Arg Glu Ala Leu Val
         50                  55                  60

Ser Val Trp Leu Gln Cys Thr Ala Ile Ser Arg Ile Tyr Thr Val Gly
 65                  70                  75                  80

Arg Ser Phe Glu Gly Arg Glu Leu Leu Val Ile Glu Leu Ser Asp Asn
                 85                  90                  95

Pro Gly Val His Glu Pro Gly Pro Glu Phe Lys Tyr Ile Gly Asn
            100                 105                 110

Met His Gly Asn Glu Ala Val Gly Arg Glu Leu Leu Ile Phe Leu Ala
            115                 120                 125

Gln Tyr Leu Cys Asn Glu Tyr Gln Lys Gly Asn Glu Thr Ile Val Asn
        130                 135                 140

Leu Ile His Ser Thr Arg Ile His Ile Met Pro Ser Leu Asn Pro Asp
145                 150                 155                 160

Gly Phe Glu Lys Ala Ala Ser Gln Pro Gly Glu Leu Lys Asp Trp Phe
                165                 170                 175

Val Gly Arg Ser Asn Ala Gln Gly Ile Asp Leu Asn Arg Asn Phe Pro
            180                 185                 190

Asp Leu Asp Arg Ile Val Tyr Val Asn Glu Lys Glu Gly Gly Pro Asn
        195                 200                 205

Asn His Leu Leu Lys Asn Met Lys Lys Ile Val Asp Gln Asn Thr Lys
    210                 215                 220
```

```
Leu Ala Pro Glu Thr Lys Ala Val Ile His Trp Ile Met Asp Ile Pro
225                 230                 235                 240

Phe Val Leu Ser Ala Asn Leu His Gly Gly Asp Leu Val Ala Asn Tyr
            245                 250                 255

Pro Tyr Asp Glu Thr Arg Ser Gly Ser Ala His Glu Tyr Ser Ser Ser
        260                 265                 270

Pro Asp Asp Ala Ile Phe Gln Ser Leu Ala Arg Ala Tyr Ser Ser Phe
    275                 280                 285

Asn Pro Ala Met Ser Asp Pro Asn Arg Pro Cys Arg Lys Asn Asp
290                 295                 300

Asp Asp Ser Ser Phe Val Asp Gly Thr Thr Asn Gly Gly Ala Trp Tyr
305                 310                 315                 320

Ser Val Pro Gly Gly Met Gln Asp Phe Asn Tyr Leu Ser Ser Asn Cys
            325                 330                 335

Phe Glu Ile Thr Val Glu Leu Ser Cys Glu Lys Phe Pro Pro Glu Glu
            340                 345                 350

Thr Leu Lys Thr Tyr Trp Glu Asp Asn Lys Asn Ser Leu Ile Ser Tyr
        355                 360                 365

Leu Glu Gln Ile His Arg Gly Val Lys Gly Phe Val Arg Asp Leu Gln
370                 375                 380

Gly Asn Pro Ile Ala Asn Ala Thr Ile Ser Val Glu Gly Ile Asp His
385                 390                 395                 400

Asp Val Thr Ser Ala Lys Asp Gly Asp Tyr Trp Arg Leu Leu Ile Pro
            405                 410                 415

Gly Asn Tyr Lys Leu Thr Ala Ser Ala Pro Gly Tyr Leu Ala Ile Thr
            420                 425                 430

Lys Lys Val Ala Val Pro Tyr Ser Pro Ala Ala Gly Val Asp Phe Glu
            435                 440                 445

Leu Glu Ser Phe Ser Glu Arg Lys Glu Glu Lys Glu Glu Leu Met
    450                 455                 460

Glu Trp Trp Lys Met Met Ser Glu Thr Leu Asn Phe
465                 470                 475
```

<210> SEQ ID NO: 3
<211> LENGTH: 476
<212> TYPE: PRT
<213> ORGANISM: Rattus sp.
<220> FEATURE:
<223> OTHER INFORMATION: carboxypeptidase E

<400> SEQUENCE: 3

```
Met Ala Gly Arg Gly Arg Val Leu Leu Ala Leu Cys Ala Ala Leu
1               5                   10                  15

Val Ala Gly Gly Trp Leu Leu Ala Ala Glu Ala Gln Glu Pro Gly Ala
            20                  25                  30

Pro Ala Ala Gly Met Arg Arg Arg Arg Leu Gln Gln Glu Asp Gly
            35                  40                  45

Ile Ser Phe Glu Tyr His Arg Tyr Pro Glu Leu Arg Glu Ala Leu Val
    50                  55                  60

Ser Val Trp Leu Gln Cys Thr Ala Ile Ser Arg Ile Tyr Thr Val Gly
65              70                  75                  80

Arg Ser Phe Glu Gly Arg Glu Leu Leu Val Ile Glu Leu Ser Asp Asn
            85                  90                  95

Pro Gly Val His Glu Pro Gly Pro Glu Phe Lys Tyr Ile Gly Asn
            100                 105                 110
```

```
Met His Gly Asn Glu Ala Val Gly Arg Glu Leu Leu Ile Phe Leu Ala
            115                 120                 125

Gln Tyr Leu Cys Asn Glu Tyr Gln Lys Gly Asn Glu Thr Ile Val Asn
        130                 135                 140

Leu Ile His Ser Thr Arg Ile His Ile Met Pro Ser Leu Asn Pro Asp
145                 150                 155                 160

Gly Phe Glu Lys Ala Ala Ser Gln Pro Gly Leu Lys Asp Trp Phe
                165                 170                 175

Val Gly Arg Ser Asn Ala Gln Gly Ile Asp Leu Asn Arg Asn Phe Pro
                180                 185                 190

Asp Leu Asp Arg Ile Val Tyr Val Asn Glu Lys Glu Gly Gly Pro Asn
                195                 200                 205

Asn His Leu Leu Lys Asn Leu Lys Lys Ile Val Asp Gln Asn Ser Lys
        210                 215                 220

Leu Ala Pro Glu Thr Lys Ala Val Ile His Trp Ile Met Asp Ile Pro
225                 230                 235                 240

Phe Val Leu Ser Ala Asn Leu His Gly Gly Asp Leu Val Ala Asn Tyr
                245                 250                 255

Pro Tyr Asp Glu Thr Arg Ser Gly Thr Ala His Glu Tyr Ser Ser Cys
                260                 265                 270

Pro Asp Asp Ala Ile Phe Gln Ser Leu Ala Arg Ala Tyr Ser Ser Phe
                275                 280                 285

Asn Pro Val Met Ser Asp Pro Asn Arg Pro Pro Cys Arg Lys Asn Asp
        290                 295                 300

Asp Asp Ser Ser Phe Val Asp Gly Thr Thr Asn Gly Gly Ala Trp Tyr
305                 310                 315                 320

Ser Val Pro Gly Gly Met Gln Asp Phe Asn Tyr Leu Ser Ser Asn Cys
                325                 330                 335

Phe Glu Ile Thr Val Glu Leu Ser Cys Glu Lys Phe Pro Pro Glu Glu
                340                 345                 350

Thr Leu Lys Ser Tyr Trp Glu Asp Asn Lys Asn Ser Leu Ile Asn Tyr
        355                 360                 365

Leu Glu Gln Ile His Arg Gly Val Lys Gly Phe Val Arg Asp Leu Gln
370                 375                 380

Gly Asn Pro Ile Ala Asn Ala Thr Ile Ser Val Asp Gly Ile Asp His
385                 390                 395                 400

Asp Val Thr Ser Ala Lys Asp Gly Asp Tyr Trp Arg Leu Leu Val Pro
                405                 410                 415

Gly Asn Tyr Lys Leu Thr Ala Ser Ala Pro Gly Tyr Leu Ala Ile Thr
                420                 425                 430

Lys Lys Val Ala Val Pro Phe Ser Pro Ala Val Gly Val Asp Phe Glu
                435                 440                 445

Leu Glu Ser Phe Ser Glu Arg Lys Glu Glu Lys Glu Glu Leu Met
        450                 455                 460

Glu Trp Trp Lys Met Met Ser Glu Thr Leu Asn Phe
465                 470                 475

<210> SEQ ID NO: 4
<211> LENGTH: 454
<212> TYPE: PRT
<213> ORGANISM: lopam
<220> FEATURE:
<223> OTHER INFORMATION: carboxypeptidase E

<400> SEQUENCE: 4
```

-continued

```
Met Lys Gln Ile Cys Ser Ile Val Leu Leu Gly Ala Val Val Ser
 1               5                  10                 15

Leu Val Ser Ala Ala Gly Ser Asp Ser Glu Ile Ser Phe Glu Tyr His
             20                  25                  30

Arg Tyr Glu Glu Leu Arg Lys Ala Leu Val Ser Val Trp Leu Gln Cys
             35                  40                  45

Pro Thr Ile Ala Arg Ile Tyr Thr Ile Gly Ser Phe Glu Gly Arg
     50                  55                  60

Glu Leu Leu Val Leu Glu Met Ser Asp Asn Pro Gly Thr His Glu Pro
 65                  70                  75                  80

Gly Glu Pro Glu Phe Lys Tyr Ile Ala Asn Met His Gly Asn Glu Ala
             85                  90                  95

Val Gly Arg Glu Leu Leu Ile Tyr Leu Ala Gln Tyr Leu Cys Asn Gln
            100                 105                 110

Tyr Gln Gln Gly Asn Glu Thr Ile Ile Asp Leu Ile His Ser Thr Arg
            115                 120                 125

Ile His Leu Met Pro Ser Met Asn Pro Asp Gly Phe Glu Lys Ala Ala
130                 135                 140

Ser Gln Pro Gly Glu Ile Lys Asp Trp Phe Val Gly Arg Ser Asn Ala
145                 150                 155                 160

Gln Gly Val Asp Leu Asn Arg Asn Phe Pro Asp Leu Asp Arg Ile Ile
                165                 170                 175

Tyr Thr Asn Glu Arg Glu Gly Gly Ala Asn Asn His Leu Leu Gln Asn
            180                 185                 190

Met Lys Lys Ala Val Asp Glu Asn Thr Lys Leu Ala Pro Glu Thr Lys
        195                 200                 205

Ala Val Ile His Trp Ile Met Glu Ile Pro Phe Val Leu Ser Ala Asn
210                 215                 220

Leu His Gly Gly Asp Val Val Ala Asn Tyr Pro Tyr Asp Glu Thr Arg
225                 230                 235                 240

Thr Gly Ser Thr His Glu Tyr Ser Ala Ser Pro Asp Asp Val Ile Phe
                245                 250                 255

Lys Ser Leu Ala Lys Ala Phe Ser Ile Tyr Asn Pro Val Met Ser Asp
            260                 265                 270

Pro Gln Arg Pro Pro Cys Arg Lys His Asp Asp Ser Ser Phe Lys
        275                 280                 285

Asp Gly Ile Thr Asn Gly Gly Ala Trp Tyr Ser Val Pro Gly Gly Met
290                 295                 300

Gln Asp Phe Asn Tyr Leu Ser Ser Asn Cys Phe Glu Ile Thr Leu Glu
305                 310                 315                 320

Leu Ser Cys Asp Lys Phe Pro Asn Glu Asp Thr Leu Lys Thr Tyr Trp
                325                 330                 335

Glu Gln Asn Arg Asn Ser Leu Val Asn Tyr Ile Glu Gln Val His Arg
            340                 345                 350

Gly Val Lys Gly Tyr Val Arg Asp Leu Gln Gly Asn Pro Ile Phe Asn
            355                 360                 365

Ala Thr Ile Ser Val Glu Gly Ile Asp His Asp Ile Thr Thr Ala Lys
        370                 375                 380

Asp Gly Asp Tyr Trp Arg Leu Leu Arg Gln Gly Asn Tyr Lys Val Ala
385                 390                 395                 400

Ala Ser Ala Pro Gly Tyr Leu Thr Val Ile Lys Lys Val Ala Val Pro
                405                 410                 415

His Ser Pro Ala Thr Arg Val Asp Phe Glu Leu Glu Ser Leu Met Glu
```

```
                     420             425             430
Arg Lys Glu Glu Arg Glu Glu Leu Met Asp Trp Trp Lys Met Met
            435             440             445
Ser Glu Thr Leu Asn Phe
            450
```

<210> SEQ ID NO: 5
<211> LENGTH: 561
<212> TYPE: PRT
<213> ORGANISM: bovine
<220> FEATURE:
<223> OTHER INFORMATION: carboxypeptidase E

<400> SEQUENCE: 5

```
Met Asp Thr Ser Lys Met Leu Ser Gln Cys Val Leu Val Phe Ala Ala
  1               5                  10                  15
Ala Val Ala Ile Val Ser Tyr Gln Ser Ile Glu Ala Ser Gln Asp Thr
                 20                  25                  30
Glu Glu Asn Gly Ser Lys Lys Pro Glu Ser Thr Ile Phe Phe His His
             35                  40                  45
Thr Tyr Glu Glu Met Val Ser Leu Met Tyr Glu Val Asn Lys Ala Cys
         50                  55                  60
Pro Glu Val Thr Arg Ile Tyr Asn Leu Ser Glu Pro Ser Val Glu Lys
 65                  70                  75                  80
Arg Asn Leu Thr Val Leu Glu Ile Thr Glu Asn Pro Gly Val His Val
                 85                  90                  95
Pro Gly Lys Pro Glu Phe Lys Tyr Val Ala Asn Met His Gly Asn Glu
            100                 105                 110
Val Val Gly Lys Glu Met Val Leu Tyr Phe Leu Val Ala Leu Cys Glu
        115                 120                 125
Glu Tyr Lys Arg Gly Asp Lys Leu Ala Asn Phe Ile Val Ser Gln Thr
    130                 135                 140
Arg Val His Val Leu Pro Ser Met Asn Pro Asp Gly Trp Gln Lys Ala
145                 150                 155                 160
Tyr Lys Glu Leu Gln Glu Lys Gly Glu Ala Gly Trp Leu Thr Gly Arg
                165                 170                 175
Ala Asn Ala Asn Asp Val Asp Leu Asn Arg Asn Phe Pro Asp Leu Asn
            180                 185                 190
Ala Gln Ile Tyr Glu Asn Glu Lys Lys His Lys Gly Arg Asn Asn His
        195                 200                 205
Leu Val Lys Val Glu Asn Thr Ile Ala Asn Asp Lys Ser Leu Gln Pro
    210                 215                 220
Glu Thr Arg Ala Val Met Arg Trp Phe Ala Glu Ile Gly Phe Val Leu
225                 230                 235                 240
Ser Ser Asn Leu His Gly Gly Asp Leu Val Ala Asn Tyr Pro Tyr Asp
                245                 250                 255
Glu Thr Arg Ser Gly Lys Met Gln Glu Tyr Thr Ala Cys Pro Asp Asp
            260                 265                 270
His Thr Phe Val Tyr Leu Ala Lys Ser Tyr Ala Tyr Phe His Ala Thr
        275                 280                 285
Met Ala Asp Pro Glu Arg Pro Cys Asp Lys Asp Gly Asp Asn Lys
        290                 295                 300
Pro Ile Thr Asn Gly Gly Leu Trp Tyr Ser Val Ala Arg Gly Met Gln
305                 310                 315                 320
Asp Tyr Asn Tyr Leu Asn Thr Asn Cys Phe Glu Ile Thr Leu Glu Leu
```

325                     330                         335
      Gly Cys Lys Lys Phe Pro Ala Ala Ser Glu Leu Glu Lys Tyr Trp Leu
                      340                     345                 350

Asp Asn Ala Ala Ile Tyr Asn Tyr Val Leu Gln Thr His Ile Gly
                  355                     360                 365

Val Lys Gly Phe Val Lys Ser Val Asp Asp Thr Pro Ile Ala Asn Ala
          370                     375                 380

Glu Ile Lys Val Arg Ser Leu Ala Thr Gly Phe Pro Ile Asp His Asp
      385                     390                 395                 400

Ile Val Ser Leu Glu Asp Gly Asp Tyr Tyr Arg Leu Leu Gly Asn Gly
                          405                 410                 415

Tyr Tyr His Ile Gln Ala Lys Ala Glu Gly Phe His Pro Arg Ser Lys
                      420                 425                 430

Cys Ile Arg Ile Glu Asn Asn Ile His Val Gly Val Pro Ser Tyr Asp
                      435                 440                 445

Leu Arg Pro Ala Thr Gln Met Asn Phe Thr Leu Asn Pro Thr Lys Leu
          450                     455                 460

Pro Gln Glu Ser Asp Lys Lys Glu Asp Tyr Asn Cys Glu Arg Leu Trp
      465                     470                 475                 480

Asn Glu Val Gln Met Glu Thr Gln Leu Glu Asp Arg Glu Leu Leu Val
                          485                 490                 495

Ser Val Leu Ser Tyr Leu Gln Pro Gln Thr Lys Trp Ser Leu Leu Ala
                      500                 505                 510

Asp Gln Leu Ser Thr Leu Glu Leu Tyr Ser Leu Leu Ala Glu Ala Leu
                  515                 520                 525

Lys Glu Leu Asn Pro Asp Gln Met Arg Glu Val Leu Glu Arg Leu Pro
      530                 535                 540

His Ala Val Gln Glu Gln Leu Glu Leu Val Ile Ser Ala His Met Ser
      545                 550                 555                 560

Lys

<210> SEQ ID NO: 6
      <211> LENGTH: 476
      <212> TYPE: PRT
      <213> ORGANISM: Murinae gen. sp.
      <220> FEATURE:
      <223> OTHER INFORMATION: carboxypeptidase E

<400> SEQUENCE: 6

Met Ala Gly Arg Gly Arg Val Leu Leu Ala Leu Cys Ala Ala Leu
      1               5                   10                  15

Val Ala Gly Gly Trp Leu Leu Thr Ala Glu Ala Gln Glu Pro Gly Ala
                      20                  25                  30

Pro Ala Ala Gly Met Arg Arg Arg Arg Leu Gln Gln Glu Asp Gly
                  35                  40                  45

Ile Ser Phe Glu Tyr His Arg Tyr Pro Glu Leu Arg Glu Ala Leu Val
          50                  55                  60

Ser Val Trp Leu Gln Cys Thr Ala Ile Ser Arg Ile Tyr Thr Val Gly
      65                  70                  75                  80

Arg Ser Phe Glu Gly Arg Glu Leu Leu Val Ile Glu Leu Ser Asp Asn
                      85                  90                  95

Pro Gly Val His Glu Pro Gly Glu Pro Glu Phe Lys Tyr Ile Gly Asn
                  100                 105                 110

Met His Gly Asn Glu Ala Val Gly Arg Glu Leu Leu Ile Phe Leu Ala
              115                 120                 125

-continued

```
Gln Tyr Leu Cys Asn Glu Tyr Gln Lys Gly Asn Glu Thr Ile Val Asn
        130                 135                 140

Leu Ile His Ser Thr Arg Ile His Ile Met Pro Ser Leu Asn Pro Asp
145                 150                 155                 160

Gly Phe Glu Lys Ala Ala Ser Gln Pro Gly Glu Leu Lys Asp Trp Phe
                165                 170                 175

Val Gly Arg Ser Asn Ala Gln Gly Ile Asp Leu Asn Arg Asn Phe Pro
            180                 185                 190

Asp Leu Asp Arg Ile Val Tyr Val Asn Glu Lys Glu Gly Gly Pro Asn
        195                 200                 205

Asn His Leu Leu Lys Asn Leu Lys Lys Ile Val Asp Gln Asn Ser Lys
    210                 215                 220

Leu Ala Pro Glu Thr Lys Ala Val Ile His Trp Ile Met Asp Ile Pro
225                 230                 235                 240

Phe Val Leu Ser Ala Asn Leu His Gly Gly Asp Leu Val Ala Asn Tyr
                245                 250                 255

Pro Tyr Asp Glu Thr Arg Ser Gly Thr Ala His Glu Tyr Ser Ser Cys
            260                 265                 270

Pro Asp Asp Ala Ile Phe Gln Ser Leu Ala Arg Ala Tyr Ser Ser Phe
        275                 280                 285

Asn Pro Val Met Ser Asp Pro Asn Arg Pro Pro Cys Arg Lys Asn Asp
    290                 295                 300

Asp Asp Ser Ser Phe Val Asp Gly Thr Thr Asn Gly Gly Ala Trp Tyr
305                 310                 315                 320

Ser Val Pro Gly Gly Met Gln Asp Phe Asn Tyr Leu Ser Ser Asn Cys
                325                 330                 335

Phe Glu Ile Thr Val Glu Leu Ser Cys Glu Lys Phe Pro Pro Glu Glu
            340                 345                 350

Thr Leu Lys Ser Tyr Trp Glu Asp Asn Lys Asn Ser Leu Ile Ser Tyr
        355                 360                 365

Leu Glu Gln Ile His Arg Gly Val Lys Gly Phe Val Arg Asp Leu Gln
    370                 375                 380

Gly Asn Pro Ile Ala Asn Ala Thr Ile Ser Val Asp Gly Ile Asp His
385                 390                 395                 400

Asp Val Thr Ser Ala Lys Asp Gly Asp Tyr Trp Arg Leu Leu Ala Pro
                405                 410                 415

Gly Asn Tyr Lys Leu Thr Ala Ser Ala Pro Gly Tyr Leu Ala Ile Thr
            420                 425                 430

Lys Lys Val Ala Val Pro Phe Ser Pro Ala Val Gly Val Asp Phe Glu
        435                 440                 445

Leu Glu Ser Phe Ser Glu Arg Lys Glu Glu Lys Glu Glu Leu Met
    450                 455                 460

Glu Trp Trp Lys Met Met Ser Glu Thr Leu Asn Phe
465                 470                 475

<210> SEQ ID NO: 7
<211> LENGTH: 434
<212> TYPE: PRT
<213> ORGANISM: alysia
<220> FEATURE:
<223> OTHER INFORMATION: carboxypeptidase E

<400> SEQUENCE: 7

Arg Pro Gln Glu Asp Gly Ile Ser Phe Glu Tyr His Arg Tyr Pro Glu
  1               5                  10                  15
```

-continued

```
Leu Arg Glu Ala Leu Val Ser Val Trp Leu Gln Cys Ala Ala Val Ser
             20                  25                  30

Arg Ile Tyr Thr Val Gly Arg Ser Phe Glu Gly Arg Glu Leu Leu Val
             35                  40                  45

Leu Glu Leu Ser Asp Asn Pro Gly Val His Glu Pro Gly Glu Pro Glu
             50                  55                  60

Phe Lys Tyr Ile Gly Asn Met His Gly Asn Glu Ala Val Gly Arg Glu
 65                  70                  75                  80

Leu Leu Ile Phe Leu Ala Gln Tyr Leu Cys Asn Glu Tyr Gln Lys Gly
                 85                  90                  95

Asn Glu Thr Ile Val Gln Leu Ile His Asn Thr Arg Ile His Ile Met
             100                 105                 110

Pro Ser Leu Asn Pro Asp Gly Phe Glu Lys Ala Ala Ser Gln Leu Gly
             115                 120                 125

Glu Leu Lys Asp Trp Phe Val Gly Arg Ser Asn Ala Gln Gly Ile Asp
             130                 135                 140

Leu Asn Arg Asn Phe Pro Asp Leu Asp Arg Ile Val Tyr Ile Asn Glu
145                 150                 155                 160

Lys Glu Gly Gly Pro Asn Asn His Leu Leu Lys Asn Leu Lys Lys Ile
                 165                 170                 175

Val Asp Gln Asn Thr Lys Leu Ala Pro Glu Thr Lys Ala Val Ile His
             180                 185                 190

Trp Ile Met Asp Ile Pro Phe Val Leu Ser Ala Asn Leu His Gly Gly
             195                 200                 205

Asp Leu Val Ala Asn Tyr Pro Tyr Asp Glu Thr Arg Ser Gly Ser Ala
             210                 215                 220

His Glu Tyr Ser Ser Cys Pro Asp Asp Ile Phe Gln Ser Leu Ala
225                 230                 235                 240

Arg Ala Tyr Ser Ser Phe Asn Pro Pro Met Ser Asp Pro Asp Arg Pro
                 245                 250                 255

Pro Cys Arg Lys Asn Asp Asp Ser Ser Phe Val Glu Gly Thr Thr
             260                 265                 270

Asn Gly Ala Ala Trp Tyr Ser Val Pro Gly Gly Met Gln Asp Phe Asn
             275                 280                 285

Tyr Leu Ser Ser Asn Cys Phe Glu Ile Thr Val Glu Leu Ser Cys Glu
             290                 295                 300

Lys Phe Pro Pro Glu Glu Thr Leu Lys Asn Tyr Trp Glu Asp Asn Lys
305                 310                 315                 320

Asn Ser Leu Ile Ser Tyr Ile Gln Gln Ile His Arg Gly Val Lys Gly
                 325                 330                 335

Phe Val Arg Asp Leu Gln Gly Asn Pro Ile Ala Asn Ala Thr Leu Ser
             340                 345                 350

Val Glu Gly Ile Asp His Asp Val Thr Ser Ala Lys Asp Gly Asp Tyr
             355                 360                 365

Trp Arg Leu Leu Val Pro Gly Asn Tyr Lys Leu Thr Ala Ser Ala Pro
             370                 375                 380

Gly Tyr Leu Ala Ile Ala Lys Lys Val Ala Val Pro Tyr Ser Pro Ala
385                 390                 395                 400

Val Arg Val Asp Phe Glu Leu Glu Ser Phe Ser Glu Arg Lys Glu Glu
                 405                 410                 415

Glu Lys Glu Glu Leu Met Glu Trp Trp Lys Met Met Ser Glu Thr Leu
             420                 425                 430
```

-continued

Asn Phe

```
<210> SEQ ID NO: 8
<211> LENGTH: 439
<212> TYPE: PRT
<213> ORGANISM: Homo sapiens
<220> FEATURE:
<223> OTHER INFORMATION: carboxypeptidase homolog -- CPM

<400> SEQUENCE: 8
```

Gly Leu Trp Leu Gly Leu Leu Pro Leu Val Ala Ala Leu Asp Phe
 1               5                  10                  15

Asn Tyr His Arg Gln Glu Gly Met Glu Ala Phe Leu Lys Thr Val Ala
                20                  25                  30

Gln Asn Tyr Ser Ser Val Thr His Leu His Ser Ile Gly Lys Ser Val
            35                  40                  45

Lys Gly Arg Asn Leu Trp Val Leu Val Val Gly Arg Phe Pro Lys Glu
        50                  55                  60

His Arg Ile Gly Ile Pro Glu Phe Lys Tyr Val Ala Asn Met His Gly
 65                  70                  75                  80

Asp Glu Thr Val Gly Arg Glu Leu Leu Leu His Leu Ile Asp Tyr Leu
                85                  90                  95

Val Thr Ser Asp Gly Lys Asp Pro Glu Ile Thr Asn Leu Ile Asn Ser
            100                 105                 110

Thr Arg Ile His Ile Met Pro Ser Met Asn Pro Asp Gly Phe Glu Ala
        115                 120                 125

Val Lys Lys Pro Asp Cys Tyr Tyr Ser Ile Gly Arg Glu Asn Tyr Asn
    130                 135                 140

Gln Tyr Asp Leu Asn Arg Asn Phe Pro Asp Ala Phe Glu Tyr Asn Asn
145                 150                 155                 160

Val Ser Arg Gln Pro Glu Thr Val Ala Val Met Lys Trp Leu Lys Thr
                165                 170                 175

Glu Thr Phe Val Leu Ser Ala Asn Leu His Gly Gly Ala Leu Val Ala
            180                 185                 190

Ser Tyr Pro Phe Asp Asn Gly Val Gln Ala Thr Gly Ala Leu Tyr Ser
        195                 200                 205

Arg Ser Leu Thr Pro Asp Asp Val Phe Gln Tyr Leu Ala His Thr
    210                 215                 220

Tyr Ala Ser Arg Asn Pro Asn Met Lys Lys Gly Asp Glu Cys Lys Asn
225                 230                 235                 240

Lys Met Asn Phe Pro Asn Gly Val Thr Asn Gly Tyr Ser Trp Tyr Pro
                245                 250                 255

Leu Gln Gly Gly Met Gln Asp Tyr Asn Tyr Ile Trp Ala Gln Cys Phe
            260                 265                 270

Glu Ile Thr Leu Glu Leu Ser Cys Cys Lys Tyr Pro Arg Glu Glu Lys
        275                 280                 285

Leu Pro Ser Phe Trp Asn Asn Asn Lys Ala Ser Leu Ile Glu Tyr Ile
    290                 295                 300

Lys Gln Val His Leu Gly Val Lys Gly Gln Val Phe Asp Gln Asn Gly
305                 310                 315                 320

Asn Pro Leu Pro Asn Val Ile Val Glu Val Gln Asp Arg Lys His Ile
                325                 330                 335

Cys Pro Tyr Arg Thr Asn Lys Tyr Gly Glu Tyr Tyr Leu Leu Leu Leu
            340                 345                 350

Pro Gly Ser Tyr Ile Ile Asn Val Thr Val Pro Gly His Asp Pro His

```
            355                 360                 365
Ile Thr Lys Val Ile Ile Pro Glu Lys Ser Gln Asn Phe Ser Ala Leu
        370                 375                 380

Lys Lys Asp Ile Leu Leu Pro Phe Gln Gly Gln Leu Asp Ser Ile Pro
385                 390                 395                 400

Val Ser Asn Pro Ser Cys Pro Met Ile Pro Leu Tyr Arg Asn Leu Pro
                405                 410                 415

Asp His Ser Ala Ala Thr Lys Pro Ser Leu Phe Leu Phe Leu Val Ser
                420                 425                 430

Leu Leu His Ile Phe Phe Lys
                435

<210> SEQ ID NO: 9
<211> LENGTH: 458
<212> TYPE: PRT
<213> ORGANISM: Homo sapiens
<220> FEATURE:
<223> OTHER INFORMATION: carboxypeptidase homolog -- CPN

<400> SEQUENCE: 9

Met Ser Asp Leu Leu Ser Val Phe Leu His Leu Leu Leu Phe Lys
 1               5                  10                  15

Leu Val Ala Pro Val Thr Phe Arg His His Arg Tyr Asp Asp Leu Val
                20                  25                  30

Arg Thr Leu Tyr Lys Val Gln Asn Glu Cys Pro Gly Ile Thr Arg Val
            35                  40                  45

Tyr Ser Ile Gly Arg Ser Val Glu Gly Arg His Leu Tyr Val Leu Glu
        50                  55                  60

Phe Ser Asp His Pro Gly Ile His Glu Pro Leu Glu Pro Glu Val Lys
65                  70                  75                  80

Tyr Val Gly Asn Met His Gly Asn Glu Ala Leu Gly Arg Glu Leu Met
                85                  90                  95

Leu Gln Leu Ser Glu Phe Leu Cys Glu Glu Phe Arg Asn Arg Asn Gln
            100                 105                 110

Arg Ile Val Gln Leu Ile Gln Asp Thr Arg Ile His Ile Leu Pro Ser
        115                 120                 125

Met Asn Pro Asp Gly Tyr Glu Val Ala Ala Gln Gly Pro Asn Lys
130                 135                 140

Pro Gly Tyr Leu Val Gly Arg Asn Asn Ala Asn Gly Val Asp Leu Asn
145                 150                 155                 160

Arg Asn Phe Pro Asp Leu Asn Thr Tyr Ile Tyr Tyr Asn Glu Lys Tyr
                165                 170                 175

Gly Gly Pro Asn His His Leu Pro Leu Pro Asp Asn Trp Lys Ser Gln
            180                 185                 190

Val Glu Pro Glu Thr Arg Ala Val Ile Arg Trp Met His Ser Phe Asn
        195                 200                 205

Phe Val Leu Ser Ala Asn Leu His Gly Gly Ala Val Val Ala Asn Tyr
    210                 215                 220

Pro Tyr Asp Lys Ser Phe Glu His Arg Val Arg Gly Val Arg Arg Thr
225                 230                 235                 240

Ala Ser Thr Pro Thr Pro Asp Asp Lys Leu Phe Gln Lys Leu Ala Lys
                245                 250                 255

Val Tyr Ser Tyr Ala His Gly Trp Met Phe Gln Gly Trp Asn Cys Gly
            260                 265                 270

Asp Tyr Phe Pro Asp Gly Ile Thr Asn Gly Ala Ser Trp Tyr Ser Leu
```

```
                275                 280                     285
Ser Lys Gly Met Gln Asp Phe Asn Tyr Leu His Thr Asn Cys Phe Glu
    290                 295                 300

Ile Thr Leu Glu Leu Ser Cys Asp Lys Phe Pro Glu Glu Glu Leu
305                 310                 315                 320

Gln Arg Glu Trp Leu Gly Asn Arg Glu Ala Leu Ile Gln Phe Leu Glu
                325                 330                 335

Gln Val His Gln Gly Ile Lys Gly Met Val Leu Asp Glu Asn Tyr Asn
            340                 345                 350

Asn Leu Ala Asn Ala Val Ile Ser Val Ser Gly Ile Asn His Asp Val
            355                 360                 365

Thr Ser Gly Asp His Gly Asp Tyr Phe Arg Leu Leu Leu Pro Gly Ile
370                 375                 380

Tyr Thr Val Ser Ala Thr Ala Pro Gly Tyr Asp Pro Glu Thr Val Thr
385                 390                 395                 400

Val Thr Val Gly Pro Ala Glu Pro Thr Leu Val Asn Phe His Leu Lys
                405                 410                 415

Arg Ser Ile Pro Gln Val Ser Pro Val Arg Arg Ala Pro Ser Arg Arg
            420                 425                 430

His Gly Val Arg Ala Lys Val Gln Pro Gln Ala Arg Lys Lys Glu Met
            435                 440                 445

Glu Met Arg Gln Leu Gln Arg Gly Pro Ala
    450                 455

<210> SEQ ID NO: 10
<211> LENGTH: 641
<212> TYPE: PRT
<213> ORGANISM: Homo sapiens
<220> FEATURE:
<223> OTHER INFORMATION: carboxypeptidase homolog -- CPZ

<400> SEQUENCE: 10

Met Pro Pro Pro Leu Leu Leu Leu Thr Val Leu Val Val Ala
1               5                   10                  15

Ala Ala Arg Pro Gly Cys Glu Phe Glu Arg Asn Pro Ala Ala Thr Cys
                20                  25                  30

Val Asp Leu Gln Leu Arg Thr Cys Ser Asp Ala Ala Tyr Asn His Thr
            35                  40                  45

Thr Phe Pro Asn Leu Leu Gln His Arg Ser Trp Glu Val Val Glu Ala
    50                  55                  60

Ser Ser Glu Tyr Ile Leu Leu Ser Val Leu His Gln Leu Leu Glu Gly
65                  70                  75                  80

Gln Cys Asn Pro Asp Leu Arg Leu Leu Gly Cys Ala Val Leu Ala Pro
                85                  90                  95

Arg Cys Glu Gly Gly Trp Val Arg Pro Cys Arg His Ile Cys Glu
                100                 105                 110

Gly Leu Arg Glu Val Cys Gln Pro Ala Phe Asp Ala Ile Asp Met Ala
            115                 120                 125

Trp Pro Tyr Phe Leu Asp Cys His Arg Tyr Phe Thr Arg Glu Asp Glu
    130                 135                 140

Gly Cys Tyr Asp Pro Leu Glu Lys Leu Arg Gly Gly Leu Glu Ala Asp
145                 150                 155                 160

Glu Ala Leu Pro Ser Gly Leu Pro Pro Thr Phe Ile Arg Phe Ser His
                165                 170                 175

His Ser Tyr Ala Gln Met Val Arg Val Leu Arg Arg Thr Ala Ser Arg
```

```
                180                 185                 190
Cys Ala His Val Ala Arg Thr Tyr Ser Ile Gly Arg Ser Phe Asp Gly
            195                 200                 205
Arg Glu Leu Leu Val Ile Glu Phe Ser Ser Arg Pro Gly Gln His Glu
210                 215                 220
Leu Met Glu Pro Glu Val Lys Leu Ile Gly Asn Ile His Gly Asn Glu
225                 230                 235                 240
Val Ala Gly Arg Glu Met Leu Ile Tyr Leu Ala Gln Tyr Leu Cys Ser
            245                 250                 255
Glu Tyr Leu Leu Gly Asn Pro Arg Ile Gln Arg Leu Leu Asn Thr Thr
            260                 265                 270
Arg Ile His Leu Leu Pro Ser Ile Asn Pro Asp Gly Tyr Glu Val Ala
            275                 280                 285
Ala Ala Glu Gly Ala Gly Tyr Asn Gly Trp Thr Ser Gly Arg Gln Asn
            290                 295                 300
Ala Gln Asn Leu Asp Leu Asn Arg Asn Phe Pro Asp Leu Thr Ser Glu
305                 310                 315                 320
Tyr Tyr Arg Leu Ala Glu Thr Arg Gly Ala Arg Ser Asp His Ile Pro
            325                 330                 335
Ile Pro Gln His Tyr Trp Trp Gly Lys Val Ala Pro Glu Thr Lys Ala
            340                 345                 350
Ile Met Lys Trp Met Gln Thr Ile Pro Phe Val Leu Ser Ala Ser Leu
            355                 360                 365
His Gly Gly Asp Leu Val Val Ser Tyr Pro Phe Asp Phe Ser Lys His
            370                 375                 380
Pro Gln Glu Glu Lys Met Phe Ser Pro Thr Pro Asp Glu Lys Met Phe
385                 390                 395                 400
Lys Leu Leu Ser Arg Ala Tyr Ala Asp Val His Pro Met Met Met Asp
            405                 410                 415
Arg Ser Glu Asn Arg Cys Gly Gly Asn Phe Leu Lys Arg Gly Ser Ile
            420                 425                 430
Ile Asn Gly Ala Asp Trp Tyr Ser Phe Thr Gly Gly Met Ser Asp Phe
            435                 440                 445
Asn Tyr Leu His Thr Asn Cys Phe Glu Ile Thr Val Glu Leu Gly Cys
450                 455                 460
Val Lys Phe Pro Pro Glu Glu Ala Leu Tyr Thr Leu Trp Gln His Asn
465                 470                 475                 480
Lys Glu Ser Leu Leu Asn Phe Val Glu Thr Val His Arg Gly Ile Lys
            485                 490                 495
Gly Val Val Thr Asp Lys Phe Gly Lys Pro Val Lys Asn Ala Arg Ile
            500                 505                 510
Ser Val Lys Gly Ile Arg His Asp Ile Thr Thr Ala Pro Asp Gly Asp
            515                 520                 525
Tyr Trp Arg Leu Leu Pro Pro Gly Ile His Ile Val Ile Ala Gln Ala
            530                 535                 540
Pro Gly Tyr Ala Lys Val Ile Lys Lys Val Ile Pro Ala Arg Met
545                 550                 555                 560
Lys Arg Ala Gly Arg Val Asp Phe Ile Leu Gln Pro Leu Gly Met Gly
            565                 570                 575
Pro Lys Asn Phe Ile His Gly Leu Arg Arg Thr Gly Pro His Asp Pro
            580                 585                 590
Leu Gly Gly Ala Ser Ser Leu Gly Glu Ala Thr Glu Pro Asp Pro Leu
            595                 600                 605
```

```
Arg Ala Arg Arg Gln Pro Ser Ala Asp Gly Ser Lys Pro Trp Trp Trp
    610             615             620

Ser Tyr Phe Thr Ser Leu Ser Thr His Arg Pro Arg Trp Leu Leu Lys
625             630             635             640

Tyr
```